United States Patent

Perry et al.

Patent Number: 6,083,901
Date of Patent: Jul. 4, 2000

[54] EMULSIONS OF FRAGRANCE RELEASING SILICON COMPOUNDS

[75] Inventors: Robert J. Perry, Niskayuna; Wen P. Liao, Clifton Park, both of N.Y.

[73] Assignee: General Electric Company, Pittsfield, Mass.

[21] Appl. No.: 09/143,640

[22] Filed: Aug. 28, 1998

[51] Int. Cl.$^7$ .............................. A61K 7/46; C09K 3/00; B01F 17/00; C08J 3/02
[52] U.S. Cl. ................. 512/2; 516/76; 516/104; 516/20
[58] Field of Search .................. 512/2, 4; 516/76, 516/104, 20

[56] References Cited

U.S. PATENT DOCUMENTS

| | | |
|---|---|---|
| 2,679,496 | 5/1954 | Bunnell . |
| 3,271,305 | 9/1966 | Allen et al. . |
| 3,779,987 | 12/1973 | Razzano . |
| 4,445,641 | 5/1984 | Baker et al. . |
| 4,500,725 | 2/1985 | Yemoto et al. . |
| 4,524,018 | 6/1985 | Yemoto et al. . |
| 4,908,208 | 3/1990 | Lee et al. . |
| 5,008,115 | 4/1991 | Lee et al. . |
| 5,071,704 | 12/1991 | Fischel-Ghodsian . |
| 5,130,171 | 7/1992 | Prud'Homme et al. . |
| 5,160,494 | 11/1992 | Krzysik et al. . |
| 5,176,903 | 1/1993 | Goldberg et al. . |
| 5,185,155 | 2/1993 | Behan et al. . |
| 5,234,689 | 8/1993 | Lindauer et al. . |
| 5,324,444 | 6/1994 | Berry et al. . |
| 5,372,806 | 12/1994 | Holloway . |
| 5,387,411 | 2/1995 | Abrutyn et al. . |
| 5,387,622 | 2/1995 | Yamamoto . |
| 5,389,607 | 2/1995 | Dartnell et al. ............................ 512/3 |
| 5,449,512 | 9/1995 | Simmons . |
| 5,490,982 | 2/1996 | Siciliano . |
| 5,500,223 | 3/1996 | Behan et al. . |
| 5,508,259 | 4/1996 | Holzner et al. . |
| 5,525,555 | 6/1996 | Zank . |
| 5,525,588 | 6/1996 | Michetti . |
| 5,585,343 | 12/1996 | McGee et al. ............................ 512/1 |

FOREIGN PATENT DOCUMENTS

| | | |
|---|---|---|
| 2041964 | 9/1980 | United Kingdom . |
| WO 96/28497 | 9/1996 | WIPO . |
| WO 9628497 | 9/1996 | WIPO . |

*Primary Examiner*—Gabrielle Brouillette
*Assistant Examiner*—Monique T. Cole
*Attorney, Agent, or Firm*—Kenneth S. Wheelock; Michelle Bugbee

[57] ABSTRACT

Fragrance releasing silicon compounds either as siloxanes or silanes may be emulsified to form water-in-oil or oil-in-water emulsions. Further non-aqueous emulsions of two or more non-aqueous immiscible phases one of which contains a fragrance releasing silicon compound may be prepared by utilizing the emulsion stabilizing properties of a particulate elastomer dispersion in a volatile silicone compound.

18 Claims, No Drawings

EMULSIONS OF FRAGRANCE RELEASING SILICON COMPOUNDS

CROSS-REFERENCE TO RELATED APPLICATIONS

Not Applicable

STATEMENT REGARDING FEDERALLY FUNDED RESEARCH

Not Applicable

FIELD OF THE INVENTION

The present invention relates to emulsions of fragrance releasing silicon compounds. The fragrance releasing silicon compounds may be oligomeric or polymeric siloxane compounds that are substituted with a fragrance bearing moiety that is released upon some chemical reaction or they may be monomeric silane species that possess a fragrance bearing moiety that is released upon some chemical reaction. The emulsions of the present invention may be either water-in-oil, oil-in-water, or an emulsion of two or more immiscible non-aqueous phases.

BACKGROUND OF THE INVENTION

I. Fragrance Releasing Siloxane or Silane Materials

The slow sustained release of a fragrant molecule is a highly desirable trait in many personal care products. A number of means have been proposed and implemented to achieve this goal. Among these means are dissolving or suspending fragrant compounds in personal care emulsions (U.S. Pat. Nos. 5,525,588; 5,525,555; 5,490,982; and 5,372,806), encapsulation of a fragrant compound (U.S. Pat. Nos. 5,500,223; 5,324,444; 5,185,155; 5,176,903; and 5,130,171), dissolving a fragrant compound into a hydrophobic phase such as a silicone (U.S. Pat. Nos. 5,449,512; 5,160,494 and 5,234,689), incorporation of a fragrant compound into cross-linked polymers (U.S. Pat. Nos. 5,387,622 and 5,387,411), incorporation of fragrant compounds into permeable laminates (U.S. Pat. Nos. 5,071,704 and 5,008,115), incorporation of fragrant compounds into matrices that soften at body temperature (U.S. Pat. No. 4,908,208), incorporation of fragrant compounds into rate controlling membranes (U.S. patent 4,445,641) and derivatization of silanes with fragrant alcohols to form alkoxy silanes (U.S. Pat. Nos. 4,524,018 and 4,500,725). All of these approaches suffer from one or more of the following problems: 1) the material is not stable in a personal care formulation, 2) the material is not easy or convenient to prepare, or 3) the material does not release the fragrant compound in a slow and sustained fashion.

II. Emulsions

Silicones have many uses in a variety of fields. They have found large commercial application in products as diverse as sealants, silicone rubbers, adhesives and cosmetics. Silicone oils have been found to be particularly desirable components of cosmetic compositions because the materials impart a dry, smooth uniform feel to the cosmetic composition among other benefits such as increasing apparent luster (or shine). The general use of silicones in cosmetic formulations has been complicated somewhat by the facts that while lower molecular weight silicones impart desirable properties to a composition they are volatile and have low viscosity, while the silicones that overcome these disadvantages are undesirably viscous.

Thus when it has been desirable to utilize low viscosity silicone oils in a cosmetic application, thickening agents have been employed to increase the solution viscosity and slow down the evaporative loss of the volatile low molecular weight silicone oil. This procedure while effective has the disadvantage of decreasing the spreadability of the silicone oil and leaves a heavy greasy feel on the skin. The spreadability and dry smooth feel are properties associated with low viscosity silicone that imparts a desirable feel or hand to the composition when it is applied as a cosmetic formulation. Materials that have found application in attempting to retain the desirable properties of low molecular weight silicone oils in cosmetic compositions while reducing evaporative losses due to high volatility have been among others fatty acid esters of dextrin, fatty acid esters of sucrose, trimethylsilyl substituted polyvinyl alcohols, trimethylsilyl substituted polysaccharides, cellulose ethers containing fatty acid esters, and organically modified clay minerals. These materials have the disadvantage that the light feeling and spreadability imparted by the low viscosity silicone oil is changed with the result that the composition no longer possesses those properties that suggested the use of the low viscosity silicone oil in the first place. Another disadvantage of these thickening agents or volatility inhibitors is that a large number of them are water soluble and must be used as a water dispersions or solutions. With hydrophobic silicone oils the introduction of water thus necessitates the use of emulsifiers and compatibilizers, complicating the formulation of the cosmetic and generally lowering the stability of the formulation with respect to separation of the component phases.

Recently, another approach to retaining the properties of low viscosity silicone oils in cosmetic compositions has been advanced where the low viscosity silicone oil is combined with the addition polymerization product between an organohydrogen polysiloxane and an alkenyl functionalized organopolysiloxane (U.S. Pat. No. 4,987,169). The organohydrogen polysiloxane utilized in those formulations comprised $HSiO_{1.5}$ ($T^H$), $RSiO_{1.5}$ (T), RHSiO ($D^H$), $R_2SiO$ (D), $R_2HSiO_{0.5}$ ($M^H$) and $R_3SiO_{0.5}$ (M) groups. The crosslinking hydride compound utilized was thus a compound of the general formula: $M_a M_b^H D_c D_d^H T_e T_f^H$. While the cross-linking compound admits T groups either as hydride or substituted by R the preference in this technology is for linear hydride materials because the addition polymerization proceeds more smoothly. The R groups in the above formulas are typical organic substituents known in the art. Subsequently a low molecular weight silicone oil is added to the cross-linked addition polymerized product and the mixture is treated by applying a shearing force. This material may be used by itself as a cosmetic component or as a thickening agent and has the properties of a grease and can be used in a wide variety of industrial lubrication applications as well as the cosmetic application contemplated. The material prepared in this manner can be regarded as a lightly cross-linked elastomer with a volatile, low molecular weight silicone oil dissolved therein. Because the precursor cross-linking hydride is preferably linear and only moderately branched when T groups are incorporated, the addition polymerized product does not possess a tight network of cross-links in the resulting polymer. Linear and lightly crosslinked networks suffer from the disadvantage of having lower efficiency in raising the viscosity of a low molecular weight silicone. In addition to increasing the cost of the product, higher levels of crosslinked silicones result in leaving behind more residue when the volatile, low molecular weight silicone evaporates during use. In some cosmetic applications, e.g. deodorant or antiperspirants, an increased residue is a significant disadvantage as it contributes to staining of the clothing.

Further, linear and lightly crosslinked silicones do not form a film as easily as more tightly crosslinked silicones. The lack of a formation of a film is a disadvantage in a cosmetic application because a film provides a softer, smoother feel as compared to the heavier, less desirable feel of a linear silicone.

For solids, size reduction processes generally result in changing both the average particle size and the particle size distribution. With most solid materials, size reduction techniques usually reduce the average particle size and produce a Gaussian distribution of particle sizes. Consequently, the art dealing with size reduction techniques is primarily concerned with controlling the width of the Gaussian distribution, i.e. how broad or how narrow the particle size distribution is, a property typically measured by the width of the distribution peak at half the peak height of the most prevalent particle size. This is typically referred to as a half-width measurement.

Emulsions can also be subjected to size reduction processes with results similar to those obtained for solid processes. An initial particle size and particle size distribution of an immiscible liquid dispersed in a second liquid phase is converted to one having a smaller average particle size. Typically the particle size distribution of the discontinuous phase in an emulsion is best represented by a Gaussian distribution regardless of whether the particle size distribution is measured before or after size reduction.

While silicones or dispersions of silicones may be emulsified to produce oil-in-water (water is the continuous phase) or water-in-oil (oil is the continuous phase) emulsions, emulsions using other extensive or continuous solvent phases typically present issues of cost and stability. Non-aqueous emulsions of silicones are useful delivery systems for cosmetic applications, particularly when the presence of water initiates a process that changes the nature of the cosmetic composition. While non-aqueous silicone emulsions are known, those utilizing lower molecular weight hydroxylic solvents such as alcohols and glycols typically have sticky or tacky feel and are thus unpleasant when applied to the skin. Further, such materials usually require the application of a high energy process to prepare the non-aqueous emulsion, e.g. homogenization, which only renders the material temporarily stable, i.e. they usually separate after only a few days.

SUMMARY OF THE INVENTION

Broadly conceived the present invention concerns the use of fragrance releasing siloxanes in mixtures to impart a desirable fragrance. The invention provides for mixtures of immiscible liquids that comprise a fragrance releasing siloxane. More particularly the invention provides for emulsions that comprise fragrance releasing siloxane. The emulsions may be conventional emulsions or microemulsions that have a haze number below an ASTM D-871 haze number of about 150. Further these emulsions may also comprise a cross linked silicone gel that has a Durometer hardness ASTM D-2240-91, of at least 5 and the gel may have a specific particle size distribution. The emulsions may be aqueous either water-in-oil or oil-in-water or they may be non-aqueous, i.e. consisting of two immiscible non-aqueous phases. A specific embodiment provides for a mixture comprising two immiscible liquid phases subject to the limitation that one of the two immiscible liquid phases comprises a fragrance releasing siloxane. A more specific embodiment provides that the fragrance releasing siloxane possess one of two formulas: firstly a fragrance releasing siloxane having the formula:

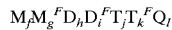

where M has the formula $R^7R^8R^9SiO_{1/2}$; $M^F$ has the formula $R^7R^8R^FSiO_{1/2}$; D has the formula $R^{10}R^{11}SiO_{2/2}$; $D^F$ has the formula $R^{10}R^FSiO_{2/2}$; T has the formula $R^{12}SiO_{3/2}$; TF has the formula $R^FSiO_{3/2}$; and Q has the formula $SiO_{4/2}$ where $R^7$, $R^8$, $R^9$, $R^{10}$, $R^{11}$ and $R^{12}$ are each independently selected for each M, $M^F$, D, $D^F$, T and $T^F$ from the group of one to forty carbon atom monovalent alkyl or alkoxy radicals and one to forty carbon atom monovalent aryl or aryloxy radicals where the subscripts f or g are positive, and one or more of the subscripts h, i, j, k or l are positive, subject to the limitation that one of the subscripts g, i, or k is one or greater than one; where $R^F$ has the formula $(R^1O)_a(R^2O)_b(R^3O)_c(R^4)_d(R^5)_eSiR^U$ with $R^U$ a two to forty atom divalent hydrocarbon radical where $R^1O$, $R^2O$ and $R^3O$ are each independently fragrant alkoxide moieties, derived from the alcohols $R^1OH$, $R^2OH$ and $R^3OH$ wherein $R^1OH$, $R^2OH$ and $R^3OH$ are independently fragrant alcohols with $R^4$ and $R^5$ selected from the group consisting of monovalent hydrocarbon radicals having from one to forty carbon atoms and monovalent alkoxy radicals having from one to forty carbon atoms, where the subscript a has a value ranging from 1 to 3 and the subscripts b, c, d, and e have values ranging from 0 to 2 subject to the limitation that a+b+c+d+e=3; or secondly a fragrance releasing siloxane having the formula:

where M has the formula $R^7R^8R^9SiO_{1/2}$; $M^F$ has the formula $R^7R^8R^FSiO_{1/2}$; D has the formula $R^{10}R^{11}SiO_{2/2}$; $D^F$ has the formula $R^{10}R^FSiO_{2/2}$; T has the formula $R^{12}SiO_{3/2}$; $T^F$ has the formula $R^FSiO_{3/2}$; and Q has the formula $SiO_{4/2}$ where $R^7$, $R^8$, $R^9$, $R^{10}$, $R^{11}$ and $R^{12}$ are each independently selected for each M, $M^F$, D, $D^F$, T and $T^F$ from the group of one to forty carbon atom monovalent alkyl or alkoxy radicals and one to forty carbon atom monovalent aryl or aryloxy radicals where the subscripts f or g are positive, and one or more of the subscripts h, i, j, k or l are positive, subject to the limitation that one of the subscripts g, i, or k is one or greater than one; where $R^F$ has the formula $(R^1O)_a(R^2O)_b(R^3O)_c(R^4)_d(R^5)_eSiR^U$ with $R^U$ a two to forty atom divalent hydrocarbon radical, where $R^1$, $R^2$ and $R^3$ are derived from the group of fragrant esters, ketones, or aldehydes, each independently having the structure:

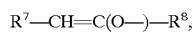

with $R^4$ and $R^5$ selected from the group consisting of monovalent hydrocarbon radical having from one to forty carbon atoms and monovalent alkoxy radicals having from one to forty carbon atoms, where the subscript a has a value ranging from 1 to 3 and the subscripts b, c, d, and e have values ranging from 0 to 2 subject to the limitation that a+b+c+d+e=3; $R^7$ is selected from the group consisting of hydrogen and monovalent hydrocarbon radicals having from one to one hundred carbon atoms and $R^8$ is selected from the group consisting of hydrogen and monovalent hydrocarbon radicals having from one to one hundred carbon atoms where the subscript a has a value ranging from 1 to 3 and the subscripts b, c, d, and e have values ranging from 0 to 2 subject to the limitation that a+b+c+d+e3.

DETAILED DESCRIPTION OF THE INVENTION

I. Preparation of Fragrance Bearing Silanes

The compounds of the present invention introduce fragrant moieties into an olefinic silane molecule. The olefinic silane molecule is capable of further reaction under hydrosilylation conditions to form a variety of siloxanes that also possess fragrant moieties. These siloxane molecules are useful in a variety of personal care compositions. The present invention is directed to new compositions of matter that are silanes that release a fragrant alcohol, ester, ketone or aldehyde upon particular subsequent chemical reactions. Typically the subsequent chemical reaction that releases the fragrant alcohol is a hydrolysis reaction. Furthermore these silanes may be reacted to form siloxanes that release a fragrant alcohol upon the same particular subsequent chemical reactions wherein the olefinic silane precursor also releases a fragrant alcohol, ester, ketone or aldehyde.

The compounds utilized by the present invention are described by the formula:

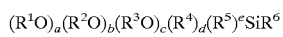

where $R^1$, $R^2$ and $R^3$ are derived from the group of alcohols consisting of $R^1OH$, $R^2OH$ and $R^3OH$ wherein $R^1OH$, $R^2OH$ and $R^3OH$ are fragrant alcohols or alternatively have the formula:

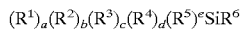

where $R^1$, $R^2$ and $R^3$ are enolate monovalent radicals derived from the group of fragrant esters, ketones, or aldehydes having the structure:

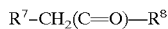

wherein the fragrant ester, ketone or aldehyde is capable of exhibiting the enol form of the carbonyl moiety under reaction conditions as shown:

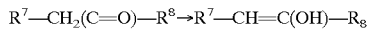

and which will react through the enol hydroxyl group to form a carbon-oxygen-silicon linkage, i.e. $R^7$—CH=C(O—)—$R^8$ where the hyphen after the oxygen in the formula indicates the species is a monovalent radical, with $R^4$ and $R^5$ selected from the group consisting of monovalent hydrocarbon radical having from one to forty carbon atoms and monovalent alkoxy radicals having from one to forty carbon atoms, $R^6$ a two to forty atom monovalent unsaturated hydrocarbon radical containing a terminal olefinic or acetylenic moiety where the subscript a has a value ranging from 1 to 3 and the subscripts b, c, d, and e have values ranging from 0 to 2 subject to the limitation that a+b+c+d+e=3; $R^7$ is selected from the group consisting of hydrogen and monovalent hydrocarbon radicals having from one to one hundred carbon atoms and $R^8$ is selected from the group consisting of hydrogen and monovalent hydrocarbon radicals having from one to one hundred carbon atoms. As used herein the phrase from one to one hundred carbon atoms is chosen wherein the class of available fragrant esters, ketones, and aldehydes is subtended by the formula $R^7$—CH$_2$(C=O)—$R^8$. As used herein, the phrase monovalent hydrocarbon radical includes both aliphatic and aromatic monovalent hydrocarbon radicals that may also include hetero-atoms such as oxygen, nitrogen, sulfur and the halogens, fluorine, chlorine, bromine and iodine.

The following synthetic examples are intended to illustrate the general synthetic reactions schemes that a person having ordinary skill in the art of silicones chemistry would typically employ in order to prepare the compounds of the present invention. These reaction schemes are thus illustrative only and do not represent the only synthetic pathways by which the compounds of the present invention may be prepared.

When the starting material is a fragrant alcohol such as phenethanol, olefinic halosilanes or olefinic silicon alkoxides may be employed as starting materials to produce the fragrance-releasing silanes of the present invention.

Reaction scheme I:

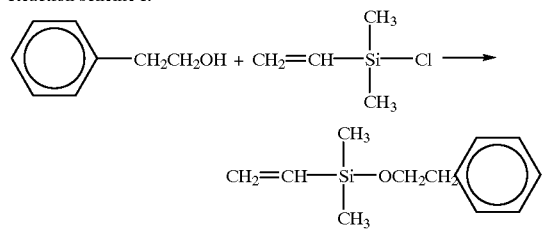

Reaction scheme II:

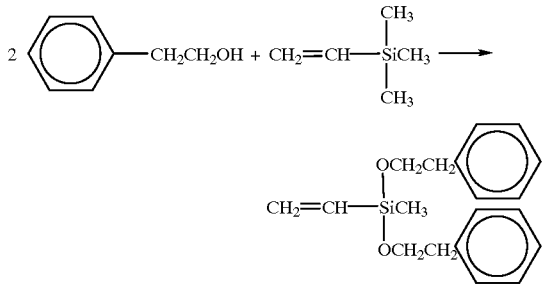

Reaction scheme III:

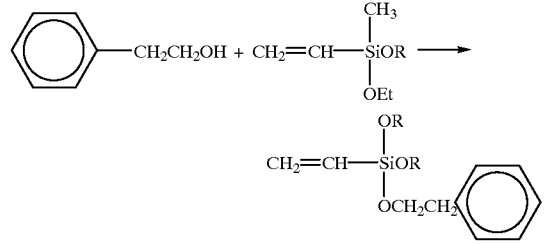

Where the R groups for reaction III may be Et ($C_2H_5$—) or —$CH_2CH_2C_6H_5$. Similarly 3-methyl-5-(2,2,3,-trimethyl-3-cyclopenten-1-yl)-4-penten-2-ol will react with chloromethylvinylsilane in a similar fashion, reaction scheme IV:

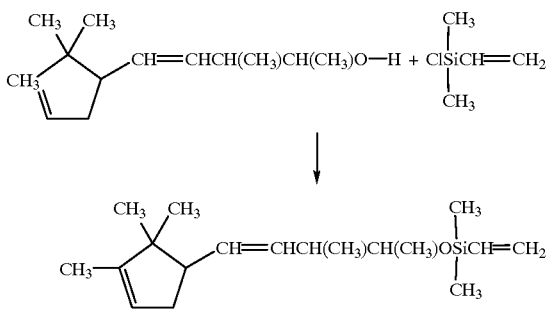

as will allyldimethylchlorosilane react with citronellol in a similar, reaction scheme V:

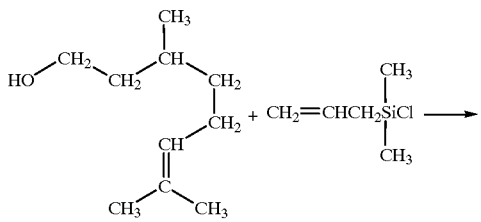

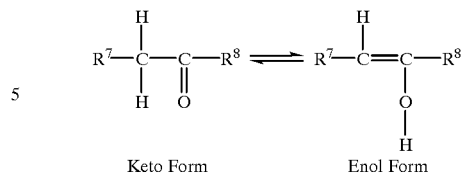

Keto Form      Enol Form

An example of the reaction scheme using a fragrant carbonyl containing moiety, 2-methyl-3-(4-t-butylphenyl)propanal, reaction VI:

Generally the equilibrium constant favors the keto form and the equilibrium lies well to the left. The extent of enolization is greatly affected by solvent, concentration and temperature. When a strong base is present, both the enol and the keto form can lose a hydrogen ion (a proton), forming an enolate anion:

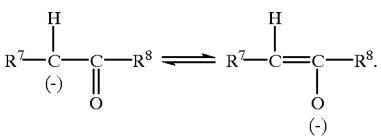

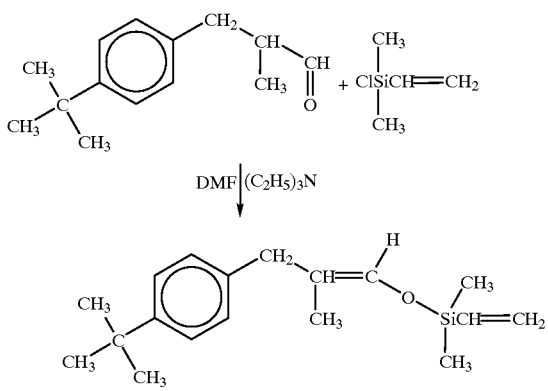

Note that DMF is dimethylformamide. Reaction scheme VI may also be used to prepare the 3-methyl-3-(3-(1-methylethylphenyl))propanal derivative:

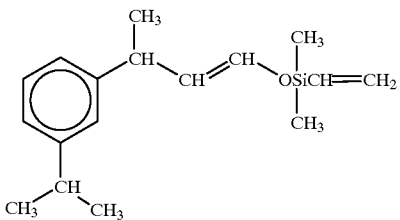

The reaction of fragrant carbonyl containing species, i.e. esters, ketones and aldehydes, requires the establishment of the keto enol tautomeric equilibrium previously referred to which is assisted by a base such as triethylamine.

Tautomerism is the chemical phenomenon of the establishment of an equilibrium between two or more structurally distinct compounds. In nearly all cases, the difference between one tautomeric form of the equilibrium compounds and the other is the isomeric placement of a hydrogen atom. A prevalent form of tautomerism is the tautomeric equilibrium established between a carbonyl compound (i.e. one containing a carbonyl group) and having a hydrogen atom alpha to the carbonyl group, i.e. an a hydrogen:

Since both of these structures differ only in the placement of electrons, these are canonical forms of the same ion rather than tautomeric isomers. Because oxygen is more electronegative than carbon, the predominate canonical form is the one where the ionic charge is more localized on the oxygen atom. While the tautomeric equilibrium between enols and ketones or aldehydes is not normally a preparative reaction, the equilibrium must occur since ketones and aldehydes often react through their enol forms as they do instantly in the preparation of the compounds of the present invention. For a more detailed explanation of this chemistry see J. March "Advanced Organic Chemistry," John Wiley & Sons, New York (1985), pp. 66–68 and 527–529 and references therein.

The fragrant alcohols that are precursors of the silanes of the present invention are selected from the group consisting of 3-methyl-5-(2,2,3, -trimethyl-3-cyclopenten-1-yl)-4-penten-2-ol, 2-methylbutanol, 3-pentanol, n-pentanol, 2-pentanol, n-hexanol, 2-methylpentanol, 1-decanol, sandela, nonadyl, dimetol, thymol, 1-heptanol, menthol, eugenol, vanillan, o-vanillan, 4-(p-hydroxyphenyl)-2-butanone, syringealdehyde, prenol, cis-3-hexanol, trans-3-hexanol, cis-4-heptenol, trans-2-octenol, trans-2-cis-6-nonadienol, geraniol, nerol, citronellol, crotyl alcohol, oleyl alcohol, linalool, α-terpineol, β-phenethyl alcohol, cinnamic alcohol, benzyl alcohol, α-methylbenzyl alcohol, nonyl alcohol, 1-octanol, 3-octanol, phenethyl salicylate, hydrocinnamyl alcohol, cis-6-nonen-1-ol, trans-2-nonen-1-ol, methyl salicylate, cis-3-octen-ol, anisyl alcohol, carvacrol, dihydrocarveol, benzyl salicylate, tetrahydrogeraniol, ethyl salicylate, ethyl vanillin, isoeugenol, isopulegol, lauryl alcohol, tetrahydrolinalool and 2-phenoxyethanol.

The fragrant carbonyl containing species are selected from the group consisting of 3-methyl-3-(3-(1-methylethylphenyl))propanal, 2-methyl-3-(4-t-butylphenyl)propanal, 3-phenylpropional, 2-phenylpropional, propional, isobutyral, 2-methylbutyral, hexanal, octanal, nonanal, decanal, 3,7-dimethyl-1-al, p-tolylacetaldehyde, phenylacetaldehyde, 4-(3)(4-methyl-3-pentenyl)-3-cyclohexen-carbaldehyde, 2,6-dimethyl-5-heptenal, 3,7-dimethyl-2,6-octadienal, trans-4-decenal, cyclamen aldehyde, 4-(p-methoxyphenyl)-2-butanone, acetophenone, 2-pentanone, 2-butanone, 2-heptanone, 3-heptanone, 2-decanone, 3-penten-2-one, 6-methyl-5-hepten-2-one, geranylacetone, ionone, 5-methyl-alpha-ionone, 2-acetonaphtone, 2-methyl-3-phenylpropan-2-yl acetate, linalyl acetate, menthanyl acetate, 2-phenylethyl acetate, tetrahydrolinalyl acetate, phenethyl propionate, phenethylhexanoate, and butyl acetate.

The fragrance releasing compounds of the present invention are particularly suited to incorporation into personal care products to impart a desirable long lasting fragrance to the products. Suitable uses include but are not limited to deodorants, antiperspirants, skin creams, facial creams, hair care products such as shampoos, mousses, styling gels, protective creams, shaving creams, after shave, cologne, perfume, color cosmetics such as lipsticks, foundations, blushes, makeup, and mascara; and other cosmetic formulations where other silicon containing components have been added and where it is desirable to impart a fragrance. Incorporation of small amounts of the compositions of the present invention into fragrance products such as shaving lotions, colognes, toilet water, and perfumes can impart a desirable long lasting fragrance to these products. Further, the silanes of the present invention may incorporated into other products where it is desirable to mask unpleasant odors with a pleasant fragrance for example household cleaning products such as waxes and polishes, automobile cleaning products such as waxes and polishes, detergents, textile coatings, paints, varnishes and the like subject to the limitation that the silane of the present invention be compatible or capable of being rendered compatible with the product in which it is incorporated.

III. Preparation of Fragrance Releasing Siloxanes that Release a Fragrant Alcohol The compounds utilized by the present invention introduce fragrant moieties via hydrosilylation of an olefinic silane molecule. These siloxane molecules are useful in a variety of personal care compositions. The present invention is directed to new compositions of matter that are siloxanes that release a fragrant alcohol upon hydrolysis.

The olefinic silanes utilized by the present invention are described by the formula:

$$(R^1O)_a(R^2O)_b(R^3O)_c(R^4)_d(R^5)_eSiR^6$$

where $R^1O$, $R^2O$ and $R^3O$ are selected (or derived from) from the group of alcohols consisting of $R^1OH$, $R^2OH$ and $R^3OH$ wherein $R^1OH$, $R^2OH$ and $R^3OH$ are fragrant alcohols with $R^4$ and $R^5$ selected from the group consisting of monovalent hydrocarbon radicals having from one to forty carbon atoms and monovalent alkoxy radicals having from one to forty carbon atoms, $R^6$ a two to forty atom monovalent unsaturated hydrocarbon radical containing a terminal olefinic or acetylenic moiety where the subscript a has a value ranging from 1 to 3 and the subscripts b, c, d, and e have values ranging from 0 to 2 subject to the limitation that a+b+c+d+e=3. As used herein, the phrase monovalent hydrocarbon radical includes both aliphatic and aromatic monovalent hydrocarbon radicals that may also include hetero-atoms such as oxygen, nitrogen, sulfur and the halogens, fluorine, chlorine, bromine and iodine.

The fragrance releasing siloxanes utilized by the present invention are prepared from an organohydrogen siloxane via conventional hydrosilylation using the fragrance bearing olefinic silane as the alkenyl source. Thus an organohydrogensiloxane having 'the formula:

$$M_fM_g^HD_hD_i^HT_jT_k^HQ_l$$

where M has the formula $R^7R^8R^9SiO_{1/2}$; $M^H$ has the formula $R^7R^8HSiO_{1/2}$; D has the formula $R^{10}R^{11}SiO_{2/2}$; DH has the formula $R^{10}HSiO_{2/2}$; T has the formula $R^{12}SiO_{3/2}$; TH has the formula $HSiO_{3/2}$; and Q has the formula $SiO_{4/2}$ where $R^7$, $R^8$, $R^9$, $R^{10}$, $R^{11}$ and $R^{12}$ are each independently selected for each M, $M^H$, D, $D^H$, and T from the group of one to forty carbon atom monovalent alkyl or alkoxy radicals and one to forty carbon atom monovalent aryl or aryloxy radicals where the subscripts f or g are positive, and one or more of the subscripts h, i, j, k or l are positive, subject to the limitation that one of the subscripts g, i, or k is one or greater than one.

The organohydrogensiloxane is reacted under hydrosilylation conditions to produce a fragrance releasing siloxane having the formula:

$$M_fM_g^FD_hD_j^FT_jT_k^FQ_l$$

where the components and subscripts satisfy the previous definitions and requirements and $M^F$ has the formula $R^7R^8R^FSiO_{1/2}$; $D^F$ has the formula $R^{10}R^FSiO_{2/2}$; and $T^F$ has the formula $R^FSiO_{3/2}$; where RF has the formula $(R^1O)_a(R^2O)_b(R^3O)_c(R^4)_d(R^5)_eSiR^U$ with $R^U$ a two to forty atom divalent hydrocarbon radical where the subscripts and components are as previously defined. This non-volatile silicone undergoes a slow hydrolysis under most conditions of use whereby the silicone releases a fragrant alcohol upon hydrolysis. This imparts a desirable odor to many different useful compositions such as cosmetics and household products.

The hydrosilylation reaction is conventionally carried out in the presence of a hydrosilylation catalyst selected from the group of ruthenium, osmium, rhodium, iridium, palladium and platinum hydrosilylation catalysts. Exemplary of such catalysts are those described in U.S. Pat. Nos. 2,823, 218; 3,159,601; 3,159,662; and 3,775,452. A non-limiting example of hydrosilylation to produce the compounds contemplated by the present invention is for instance:

(HSi(CH₃)₂O₁/₂)(Si(CH₃)₂O₂/₂)₂₃(HSi(CH₃)₂O₁/₂)
+CH₂=CHSi(CH₃)₂OCH₂CH₂Ph→
(PhCH₂CH₂OSi(CH₃)₂CH₂CH₂Si(CH₃)₂O₁/₂)₂(Si(CH₃)₂O₂/₂)₂₃

IV. Preparation of Fragrance Releasing Siloxanes that Release a Fragrant Aldehyde, Ketone or Ester The compounds of the present invention introduce fragrant moieties via hydrosilylation of an olefinic silane molecule. These siloxane molecules are useful in a variety of personal care compositions. The present invention is directed to new compositions of matter that are siloxanes that release a fragrant aldehyde, ketone or ester upon hydrolysis.

The olefinic silanes utilized by the present invention are described by the formula:

$$(R^1)_a(R^2)_b(R^3)_c(R^4)_d(R^5)_eSiR^6$$

where $R^1$, $R^2$ and $R^3$ are each enolate monovalent radicals derived from the group of fragrant esters, ketones, or aldehydes, each independently having the structure:

$$R^7-CH_2(C=O)-R^8$$

wherein the fragrant ester, ketone or aldehyde is capable of exhibiting the enol form of the carbonyl moiety under reaction conditions as shown:

$$R^7-CH_2(C=O)-R^8 \rightarrow R^7-CH=C(OH)-R^8$$

and which will react through the enol hydroxyl group to form a carbon-oxygen-silicon linkage (i.e. $R^7$—CH=C (O—)—$R^8$ where the hyphen after the oxygen in the formula indicates the species is a monovalent radical and independently describes $R^1$, $R^2$ and $R^3$), with $R^4$ and $R^5$ selected from the group consisting of monovalent hydrocarbon radical having from one to forty carbon atoms and monovalent alkoxy radicals having from one to forty carbon atoms, $R^6$ a two to forty atom monovalent unsaturated hydrocarbon radical containing a terminal olefinic or acetylenic moiety where the subscript a has a value ranging from 1 to 3 and the subscripts b, c, d, and e have values ranging from 0 to 2 subject to the limitation that a+b+c+d+e=3; $R^7$ is selected from the group consisting of hydrogen and monovalent hydrocarbon radicals having from one to one hundred carbon atoms and $R^8$ is selected from the group consisting of hydrogen and monovalent hydrocarbon radicals having from one to one hundred carbon atoms. As used herein the phrase from one to one hundred carbon atoms is chosen wherein the class of available fragrant esters, ketones, and aldehydes is subtended by the formula $R^7$—$CH_2$(C=O)—$R^8$. It should be noted that the structure:

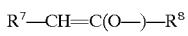

is a conjugate structure that corresponds to the enolate structure:

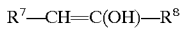

but missing the hydroxyl hydrogen. In the structure:

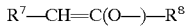

the hyphen after the oxygen atom indicates a univalent bonding site wherein the structure is a monovalent radical. As used herein, the phrase monovalent hydrocarbon radical includes both aliphatic and aromatic monovalent hydrocarbon radicals that may also include hetero-atoms such as oxygen, nitrogen, sulfur and the halogens, fluorine, chlorine, bromine and iodine.

The fragrance releasing siloxanes of the present invention are prepared from an organohydrogen siloxane via conventional hydrosilylation using the fragrance bearing olefinic silane as the alkenyl source, an example of this reaction being:

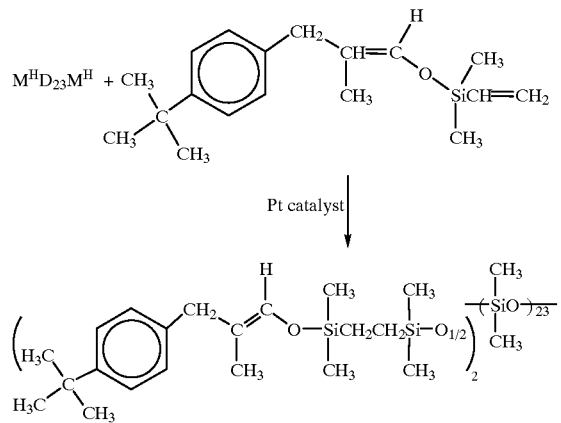

In this specific instance, $M^H$ has the formula $R^7R^8HSiO_{1/2}$ and D has the formula $R^{10}R^{11}SiO_{2/2}$ where $R^7$, $R^8$, $R^{10}$, and $R^{11}$ are all methyl groups.

Thus an organohydrogensiloxane having the formula:

where M has the formula $R^7R^8R^9SiO_{1/2}$; $M^H$ has the formula $R^7R^8HSiO_{1/2}$; D has the formula $R^{10}R^{11}SiO_{2/2}$; DH has the formula $R^{10}HSiO_{2/2}$; T has the formula $R^{12}SiO_{3/2}$; TH has the formula $HSiO_{3/2}$; and Q has the formula $SiO_{4/2}$ where $R^7$, $R^8$, $R^9$, $R^{10}$, $R^{11}$ and $R^{12}$ are each independently selected for each M, $M^H$, D, $D^H$, and T from the group of one to forty carbon atom monovalent alkyl or alkoxy radicals and one to forty carbon atom monovalent aryl or aryloxy radicals where the subscripts f or g are positive, and one or more of the subscripts h, i, j, k or l are positive, subject to the limitation that one of the subscripts g, i, or k is one or greater than one.

The organohydrogensiloxane is reacted under hydrosilylation conditions to produce a fragrance releasing siloxane having the formula:

where the components and subscripts satisfy the previous definitions and requirements and $M^F$ has the formula $R^7R^8R^FSiO_{1/2}$; $D^F$ has the formula $R^{10}R^FSiO_{2/2}$; and $T^F$ has the formula $R^FSiO_{3/2}$; where RF has the formula $(R^1O)_a(R^2O)_b(R^3O)_c(R^4)_d(R^5)^eSiR^U$ (or alternatively $(R^1)_a(R^2)_b(R^3)_c(R^4)_d(R^5)^eSiR^U$ if using a carbonyl based fragrance moiety, i.e. a ketone, aldehyde or ester) with Ru a two to forty atom divalent hydrocarbon radical where the subscripts and components are as previously defined.

V. Aqueous Emulsions of Fragrance Releasing Silicon Compounds

Generally techniques known in the art may be utilized to prepare conventional water-in-oil or oil-in-water emulsions of polymeric siloxanes. However when it is desired to prepare microemulsions, special techniques must be employed.

The instant invention of incorporating fragrance bearing silicon compounds into mixtures comprising amino-functional silicones is based upon the discovery that functionalized silicones such as amino functional silicones which are capable of forming microemulsions may be blended with surfactants having a high phase inversion temperature and the blend processed such that the mixture forms a microemulsion. Such microemulsions are generally transparent. By transparent applicants mean the absence of turbidity or haze wherein haze is defined by an ASTM test, specifically ASTM test number D871 using turbidity suspension standards and wherein said haze or turbidity is below an upper limit of about 150. At levels of the haze number above about 50 the microemulsions of the present invention begin to gradually change from transparent to translucent. The haze numbers of the microemulsions of the present invention range from 0 to about 150, more preferably from about 0 to about 80 and most preferably from 0 to about 50. The turbidity suspension standards used in the ASTM test D871 are available from Hellige Incorporated of Garden City, N.Y. Applicants note that pure distilled water is 0 on the haze scale.

Polyorganosiloxane microemulsions prepared by the method of the instant invention have a mean particle size of from about 0.0005 to about 0.050 microns, preferably from about 0.0010 to about 0.030 microns, and most preferably from about 0.0010 to about 0.025 microns. Generally haze and average particle size correlate with one another but they are also affected by the relative amounts of the two major components of the emulsion, the silicone oil and the water. Thus while at a constant oil to water ratio the haze and average particle size might correlate, haze by itself is not both a necessary and sufficient criterion to be an indicator of average particle size in a microemulsion unless other constraints are specified.

By microemulsifiable applicants define the term to mean capable of forming a microemulsion wherein the mean particle size of the emulsion ranges from 0.0001 microns to about 0.050 microns. By microemulsifiable silicone applicants define a silicone or a mixture of silicones that can form a microemulsion as defined by applicants herein before.

The phase inversion temperature is that temperature at which a given surfactant is equally soluble in a lipophilic and a hydrophilic phase that are co-extensive. Generally the hydrophilic phase of interest or use is water. At the phase inversion temperature, the surfactant, hydrophilic phase and lipophilic phase are in a thermodynamic state of minimum free energy. This thermodynamic state is characterized by a minimum in particle size of the emulsion formed therewith when the mixture is emulsified. Thus the phase inversion temperature has a tendency to be specific for a given composition of components. While the phase inversion temperature varies as a function of composition, when one of the two liquid phases is held constant e.g. water, the phase inversion temperature of a series of mixtures utilizing a given surfactant, water, and a variety of lipophilic phases that are immiscible with the water, the phase inversion temperature will tend to vary over a much narrower range of temperatures.

In one embodiment of the instant invention an oil surfactant mixture is prepared by blending:

(1) an amount ranging from 10 to 30 parts per hundred of the final composition of the microemulsion of a polyorganosiloxane that can be microemulsified, A(1), optionally having an amino content of from about 0.06 to about 3.0 milliequivalents per gram and comprising a silicone of the formula:

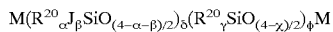

whereby in the formulas above $R^{20}$ is a hydrocarbon or hydrocarbon radical having from 1 to about 6 carbon atoms, J is a polar radical having the general formula $-R^{21}HZ$, wherein $R^{21}$ is a divalent linking group bound to hydrogen and the radical Z, comprised of carbon and hydrogen atoms; carbon hydrogen and oxygen atoms, or carbon, hydrogen and nitrogen atoms; and Z is an organic amino functional radical containing at least two amino functionalities; "α" assumes values ranging from about 0 to about 2, "β" assumes values ranging from about 1 to about 3, "α"+"β" is less than or equal to 3, and "γ" is a number in the range of from about 1 to about 3; and δ is a number in the range of from 1 to about 20 preferably from about 1 to 10 and most preferably about 8, and φ is a number in the range from about 20 to about 800, preferably from about 100 to about 500, and most preferably about 275, and M is any suitable silicone endstopping group known in the art. Non-limiting examples of radicals represented by $R^{21}$ include alkyl radicals such as methyl, ethyl, propyl, isopropyl, butyl, isobutyl, amyl, isoamyl, hexyl, isohexyl, and the like; alkenyl radicals such as vinyl, halo vinyl, alkyl vinyl, allyl, haloallyl, alkylallyl, cycloalkyl radicals such as cyclobutyl, cyclopentyl, cyclohexyl and the like, phenyl radicals, benzylradicals, halohydrocarbon radicals such as 3-chloropropyl, 4-bromobutyl, 3,3,3-trifluoropropyl, chlorocyclohexyl, bromophenyl, chlorophenyl and the like, and sulfur containing radicals such as mercaptoethyl, mercaptopropyl, mercaptohexyl, mercaptophenyl and the like; preferably $R^{21}$ is an alkyl radical containing from 1 to about 6 carbon atoms; and most preferably $R^{21}$ is methyl. Examples of $R^{21}$ include methylene, ethylene, propylene, hexamethylene, decamethylene, $-CH_2CH(CH_3)CH_2-$, phenylene, naphthylene, $-CH_2CH_2SCH_2CH_2-$, $-CH_2CH_2OCH_2-$, $-OCH_2CH_2-$, $-OCH_2CH_2CH_2-$, $-CH_2CH(CH_3)C(O)OCH_2-$, $-(CH_2)_3CC(O)OCH_2CH_2-$, $-C_6H_4C_6H_4-$, $-C_6H_4CH_2C_6H_4-$, and $-(CH_2)_3C(O)SCH_2CH_2-$.

Z is an organic amino functional radical containing at least two amino functionalities. One possible formula for Z is $-NH(CH_2)_zNH_2$ where z is one or greater. Another possible formula for Z is $-N(CH_2)_z(CH_2)_{zz}NH$ where both z and zz are independently one or greater, this structure encompasses diamino ring structures such as piperazinyl. Z is most preferably a $-NHCH_2CH_2NH_2$ radical.

J is most preferably an amine functional polar radical having the formula $-CH_2CH_2CH_2NHCH_2CH_2NH_2$.

In the formulas, "α" assumes values ranging from about 0 to about 2, "β" assumes values ranging from about 1 to about 3, "α"+"β" is less than or equal to 3, and "γ" is a number in the range of from about 1 to about 3. The molar ratio of $R^{21}{}_\alpha(Q_\beta SiO_{(4-\alpha-\beta)/2}$ units to $R^{21}{}_\gamma SiO_{(4-\gamma)/2}$ units ranges from about 1:2 to about 1:65, preferably from about 1:5 to about 1:65, and most preferably from about 1:15 to about 1:20.

It is preferred to use amino functional silicone fluids A(1) in the instant invention having the formula:

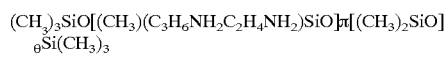

wherein π is a number in the range of from 1 to about 20 preferably from about 1 to 10 and most preferably about 8, and θ is a number in the range from about 20 to about 800, preferably from about 100 to about 500, and most preferably about 275.

(2) adding to the silicone blend from step (1), of from about 1 to 20 parts per hundred of the final composition of the microemulsion of at least one surfactant, A(3), wherein at least one of the surfactants has a high phase inversion temperature, said phase inversion temperature generally ranging from about 45 to about 95° C.;

(3) heating the blend of silicone(s) and surfactant(s) to a temperature ranging from about 45° C. to about 95° C., which is a temperature below the phase inversion temperature of the surfactant(s), while stirring;

(4) water, Part I water in the examples, in an amount equal in weight to the weight of the silicone(s) used in part 1 added slowly;

(5) adding an amount of an acid such that the final pH of the microemulsion is between about 4 and 7; preferably steps (4) and (5) are accomplished simultaneously either by the separate addition of water and a suitable acid or by the addition of an aqueous solution of a suitable acid. A preferred acid is acetic acid, however other acids may also be used such as HCl, hypophosphorous, lactic, propionic, glycolic, formic, and nitric.

(6) water, Part II water in the examples, in an amount ranging from 40 to about 90 parts, said part II water having a temperature ranging from 0° C. to about 95° C. below the temperature of acidified emulsion such that by the addition of said cold water the temperature of said microemulsion is cooled rapidly.

A(3) contains at least one surfactant, wherein at least one of the surfactants has a phase inversion temperature ranging from 50° C. to about 95° C., said surfactant hereinafter referred to as the primary surfactant. Other optional surfactants are referred to as secondary surfactants.

The surfactant or blend of surfactants has a hydrophilic-lipophilic balance value of from about 10 to about 16, preferably from about 11 to about 16, and most preferably from about 12 to about 13. The preferred hydrophilic-lipophilic balance value may vary as a consequence of increasing the level of volatile silicone in the microemulsifiable silicone.

The primary surfactant may be cationic, anionic, nonionic or amphoteric in nature. Examples of such surfactants are disclosed in U.S. Pat. No. 4,620,878 to Gee which is hereby incorporated by reference. Generally, nonionic surfactants are preferred for use in the instant invention. Surfactants useful as the primary surfactant in the instant invention include the sorbitan esters of fatty acids having 10 to 22 carbon atoms; polyoxyethylene sorbitan esters of $C_{10}$ to $C_{22}$ fatty acids having up to 95% ethylene oxide ; polyoxyethylene sorbitol esters of $C_{10}$ to $C_{22}$ fatty acids, polyoxyethylene derivatives of fatty phenols having 6 to 20 carbon atoms up to 95% ethylene oxide; fatty amino and amido betaines having 10 to 22 carbon atoms, and polyethylene condensates of $C_{10}$ to $C_{22}$ fatty acids or fatty alcohols having up to 95% ethylene oxide.

Preferred primary surfactants for the practice of the instant invention include, but are not limited to, the octylphenoxy polyethoxy ethanols, which are nonionic surfactants possessing varying amounts of ethylene oxide units and are available from Union Carbide Corporation under the general TRITON® trade name; trimethylnonyl polyethylene glycol ethers and polyethylene glycol ethers of linear 11–15 carbon atoms containing alcohols, available from Union Carbide Corporation under the general trade name TERGITOL®; the nonionic ethoxylated tridecyl ethers, available from Emery Industries under the trade name TRYCOL®.

The preferred surfactants for use as the primary surfactant of the instant invention are the trimethylnonyl polyethylene glycol ethers and polyethylene glycol ethers of linear 11–15 carbon atom containing alcohols, available from Union Carbide Corporation under the trade name TERGITOL ®. A preferred surfactant for use as the primary surfactant of the instant invention is a trimethylnonyl polyethylene glycol ether. The most preferred primary surfactant is 2,6,8-trimethyl-4-nonyloxypolyethylene oxide (TERGITOL® TMN-6)

The optional secondary surfactants may be anionic, cationic, nonionic, or amphoteric and may either be soluble or insoluble in the preferred amino functional silicone of A(1). Nonionic surfactants are preferred. Non-limiting examples of surfactants that are soluble in the amino functional silicone include the alkyl phenol ethoxylates.

Preferably, the optional secondary surfactant used in this invention is also insoluble in the silicone of A(1). The preferred surfactants for use as the secondary surfactants in the instant invention are polyethylene glycol ethers of linear 11–15 carbon atoms containing alcohols.

The amount of A(3) is in the range of from about 1 to about 30, preferably from about 1 to about 20, and most preferably from about 5 to about 15, parts by weight per 100 parts by weight of the final microemulsion composition.

The blend of silicones, surfactants and water is homogenized in a homogenizer or other suitable mixing equipment. The length of time necessary to form a homogeneous mixture or emulsion in this step will depend on mixing equipment parameters and can be determined by those skilled in the art without undue experimentation. High shear mixing, either at ambient pressure or under conditions where the reaction medium is pressurized are generally unnecessary in order to form the microemulsions of the instant invention. Because the blend contains a surfactant having a high phase inversion temperature, the temperature at which the microemulsion is formed must be carefully controlled. Thus the step of adding part I water is performed in a temperature range varying between 45° C. and 95° C., more preferably varying between 55° C. and 90° C., and most preferably varying between 65° C. and 85° C.

In step (5) the microemulsion is acidified to bring the pH of the emulsion into a range varying between 4 and 7, more preferably between 5 and 6.5, and most preferably between 5.5 and 6.5. This step is particularly effective when combined with step (4).

In order to change the pH of the reaction medium, it is necessary to consider the quantity of amino functional silicone or silicone present in the reaction mixture. The amount of acid needed to provide such pH values will depend on the amount of the amino functional silicone or silicone fluid (A)(1) and the amino content of the amino functional silicone fluid. For example, with the amino functional silicone fluid having an amino content of 0.6 milliequivalents per gram, the amount of acid sufficient to provide a pH within the desired range will be approximately 2.5 parts per weight per 100 parts per weight of the amino functional silicone fluid. With an amino functional silicone fluid having an amino content of 3.0 milliequivalents per gram, the weight of acid will be about 12.5 parts per weight per 100 parts per weight of the fluid. While the weights of acid necessary to achieve a given pH may vary depending on the molecular and equivalent weights of the acid chosen to control the pH, control of pH to the desired value is the primary purpose of the acid addition. Further, it has been found that the addition of acid must be simultaneous with the addition of the part I water.

Additionally, silicone fluids, particularly amino or ammonium functional silicone fluids, having a viscosity ranging from 10 to 10,000 centistokes at 25° C. are preferred for use with the process of the instant invention. Thus amino functional silicone fluids having an amino content ranging from about 0.10 meq./gr. to about 10.0 meq./gr. and viscosity ranging from about 10 to about 10,000 centistokes at 25° C. are preferred for use with the process of the instant invention.

The amino functional silicone microemulsions of the present invention are useful in a variety of personal care product applications such as hair conditioners, the so-called 2 in 1 shampoos, and hair fixative preparations such as styling gels mousses and the like. For purposes of personal care applications the conditioner formulations generally comprise an amino functional silicone microemulsion content ranging from about 5 weight percent to about 15 weight percent, more preferably from about 5 weight percent to about 10 weight percent, and most preferably from about 6 weight percent to about 7 weight percent. For purposes of personal care applications the 2 in 1 shampoo formulations generally comprise an amino functional silicone microemulsion content ranging from about 2 weight percent to about 7 weight percent, more preferably from about 2 weight percent to about 5 weight percent, and most preferably from about 3 weight percent to about 4 weight percent. For purposes of personal care applications the fixative formulations generally comprise an amino functional silicone microemulsion content ranging from about 2 weight percent to about 10 weight percent, more preferably from about 2 weight percent to about 6 weight percent, and most preferably from about 3 weight percent to about 5 weight percent. The personal care products utilizing microemulsions prepared by the process of the instant invention will typically exhibit haze numbers below about 100. Applicants note that the weight percent ranges herein before described constitute weight percent ranges for the finished microemulsions as a component of the personal care product. Thus a microemulsion prepared by the process of the present invention will have a silicone content varying from about 5 weight percent to about 25 weight percent, which will vary from about 0.1 weight percent to about 7 weight percent as a percentage of the final composition of the personal care product when the microemulsion is incorporated into the personal care product. Additionally, the microemulsions of the present invention may be formulated into textile treating products or skin care formulations including color cosmetics.

VI. Non-Aqueous Emulsions of Two or More Immiscible Non-Aqueous Phases

Broadly stated the present invention is based on the discovery that dispersions of silicones, particularly silicone elastomer, in various carrier solvents stabilize non-aqueous emulsions as between two immiscible non-aqueous liquid phases, one of which is hereinafter referred to as a non-aqueous solvent phase, which may or may not be the continuous phase of the emulsion. As broadly conceived the present invention provides for a non-aqueous emulsion of a silicone composition said composition comprising:

(A) a silicone and (B) a non-aqueous organic hydroxylic solvent wherein said non-aqueous emulsion comprises a continuous non-aqueous phase. One particular form of this composition involves a silicone prepared by a free radical polymerization reaction of organopolysiloxanes. A particularly preferred form of this composition involves a silicone prepared by a hydrosilylation reaction between an alkenyl silicone precursor and a hydrogen silicone precursor. Generally the alkenyl silicone precursor compound will be an organosiloxane or organopolysiloxane having two or more alkenyl groups per molecule on average and the hydrogen silicone precursor will be an organohydrogensiloxane having two or more silicon hydride groups per molecule on average. Such compounds are described in a multiplicity of U.S. patents particularly U.S. Pat. Nos. 5,506,289; 5,674,966; 5,717,010; 5,571,853; and 5,529,837 herewith specifically incorporated by reference. The alkenyl functionality and the hydride functionality may be combined into one molecule self-curing molecule or compound as is taught in U.S. Pat. No. 5,698,654. In many embodiments the silicone elastomer comprises particles which may or may not be finely divided, of elastomer dispersed in a carrier oil, preferably a silicone oil.

The composition of a specific embodiment utilized by the present invention comprises the hydrosilylation addition product of (1) a linear alkenyl stopped polyorganosiloxane having the formula:

$$M_{a'}^{vi} D_{x'} D_{y'}^{vi} M_{2-a'}$$

where the subscript x' is a number greater than 500 preferably greater than 600, more preferably greater than 700, and most preferably greater than 800, the subscript y' is a number ranging from zero to about 20, preferably ranging from zero to about 10, more preferably ranging from zero to about 5, and most preferably ranging from zero to about 4, the subscript a' is a number ranging from 0 to 2, subject to the limitation that a'+y' is within the range of from 1 to about 20, preferably from one to about 10, more preferably from about 1.5 to about 10, and most preferably from about 1.5 to about 6, with $M^{vi}$ defined as:

$$R^{31}R^{32}R^{33}SiO_{1/2}$$

where $R^{31}$ is a monovalent unsaturated hydrocarbon radical having from two to ten carbon atoms, preferably styryl, allyl and vinyl, more preferably allyl and vinyl and most preferably vinyl and $R^{32}$ and $R^{33}$ are each independently selected from the group of one to forty carbon atom monovalent hydrocarbon radicals, preferably one to twenty carbon monovalent hydrocarbon radicals, more preferably from the group consisting of methyl, ethyl, propyl, isopropyl, n-butyl, iso-butyl, sec-butyl, tert-buty, pentyl, hexyl, heptyl, phenyl, benzyl, and mesityl; and most preferably from the group consisting of methyl and phenyl with D defined as:

$$R^{34}R^{35}SiO_{2/2}$$

where $R^{34}$ and $R^{35}$ are each independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl; with $D^{vi}$ defined as:

$D^{vi}=R^{36}R^{37}SiO_{2/2}$ where $R^{36}$ is a monovalent unsaturated hydrocarbon radical having from two to ten carbon atoms, preferably styryl, allyl and vinyl, more preferably allyl and vinyl and most preferably vinyl and $R^{37}$ is independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl and with M defined as $M=R^{38}R^{39}R^{40}SiO_{1/2}$ with $R^{38}$, $R^{39}$, and $R^{40}$ each independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl and (2) a resin having the formula:

$$(M_{w'}^{H} Q_{z'})_{j'}$$

where Q has the formula $SiO_{4/2}$ and where $M^{H}$ has the formula $H_{b'}R_{3-b'}^{41}SiO_{1/2}$ with the subscript b ranging from 1 to 3, where $R^{41}$ is a one to forty carbon atom monovalent hydrocarbon radical, preferably a one to twenty carbon monovalent hydrocarbon radical, more preferably selected from the group consisting of methyl, ethyl, propyl, iso-propyl, n-butyl, iso-butyl, sec-butyl, tert-buty, pentyl, hexyl, heptyl, phenyl, benzyl, and mesityl; and most preferably selected from the group consisting of methyl and phenyl with the subscripts w' and z' having a ratio of 0.5 to 4.0 respectively, preferably 0.6 to 3.5, more preferably 0.75 to 3.0, and most preferably 1.0 to 3.0; and the subscript j' ranging from about 2.0 to about 100, preferably from about 2.0 to about 30, more preferably from about 2.0 to about 10, and most preferably from about 3.0 to about 5.0; and (3) a silicone, wherein the mixture of (3) with the reaction product of (1) and (2) has been subjected to shearing forces that affect the average particle distribution and the distribution has certain unique properties;

wherein the addition product of (1) and (2) dispersed in (3) is emulsifiable with a non-aqueous organic hydroxylic solvent.

The hydrosilylation reaction is carried out in the presence of a hydrosilylation catalyst selected from the group of ruthenium, osmium, rhodium, iridium, palladium and platinum hydrosilylation catalysts. Exemplary of such catalysts are those described in U.S. Pat. Nos. 2,823,218; 3,159,601; 3,159,662; and 3,775,452.

Applicants define the silicone, component (3), as any organo-silicon compound having a viscosity below about 1,000 centistokes at 25° C., preferably below about 500 centistokes at ° C., more preferably below about 250 centistokes at 25° C., and most preferably below 100 centistokes at 25° C. Thus low molecular weight cyclic silicones such as $D_3$, $D_4$, $D_5$, and $D_6$ (i.e. $D_f$ 'where the subscript f' ranges from 3 to 6) where D is as previously defined with $R^{34}$ and $R^{35}$ preferably methyl as well as low molecular weight linear silicones having the formula $$M'D'_iM'$$

where the substituents on D' are independently selected from the same substituents as previously defined for D and M' has the formula $$R^{42}R^{43}R^{44}SiO_{1/2}$$

where $R^{42}$, $R^{43}$ and $R^{44}$ are each independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl; and the subscript i ranges from 0 to about 300, preferably from 0 to about 100, more preferably from 0 to about 50, and most preferably from 0 to about 20 are such volatile, silicones. Preferably component (3) is a volatile low molecular weight silicone.

The materials used to prepare the gels of the present invention have been defined in terms of formulas that recite structural elements M, D, T and Q within the definitions commonly accepted in the practice of silicone chemistry. As individual molecules, or as pure compounds, the subscripts of these formulas can assume only integral values (including zero where appropriate). As complex mixtures of compounds, each of which individually satisfies the molecular definition, the subscripts in describing the mixture will assume non-integral values (including zero where appropriate). However, those non-integral values for a given subscript will still range between the upper limit and the lower limits of the range for that particular subscript when integral values are stipulated. Thus, for example in the pure compound description of component (1), the subscript a may have the values 0, 1 or 2. As a mixture of compounds, component (1) will have an average value for the subscript a that is dependent on the number of individual molecular species having a value for the subscript a that is equal to 0, 1, and 2. The same explanation holds for components (2) and (3).

Thus, the average subscripts for component (1), when component (1) is a vinyl functionalized silicone as the specific alkenyl functionalization and is a mixture of various vinyl containing compounds, as defined, will span a range of vinyl equivalent weights ranging from about 1,500 to about 150,000, preferably from about 4,500 to about 110,000, more preferably from about 10,000 to about 70,000, and most preferably from about 15,000 to about 45,000. It is to be noted that these equivalent weights are specific equivalent weights for vinyl substitution, substitution with other olefinic substituents would generate a different but comparable range of equivalent weights. Likewise, the average subscripts for component (2) as a mixture, as defined, will span a range of hydride equivalent weights ranging from about 80 to about 190, preferably from about 82 to about 170, more preferably from about 85 to about 150, and most preferably from about 87 to about 130.

Further it is desirable that the alkenyl functionality present in component (1) ranges on average of from about 2 to about 20 alkenyl groups per molecule, preferably from about 1 to about 10 alkenyl groups per molecule, more preferably from about 1.5 to about 10 alkenyl groups per molecule, and most preferably from about 1.5 to about 6 alkenyl groups per molecule. Additionally, it is desirable that the hydride functionality present in component (2) ranges on average of from about 2 to 400 SiH groups per molecule, preferably from about 8 to about 100 SiH groups per molecule, more preferably from about 8 to about 50 SiH groups per molecule, and most preferably from about 8 to about 20 SiH groups per molecule.

Components (1) and (2) (as pure compounds or mixtures) are catalytically reacted together in the presence of component (3) to produce a gel having a polymer content that is approximately from about 5 to about 75 weight percent crosslinked polymer, preferably from about 10 to about 60 weight percent crosslinked polymer, more preferably about 15 to about 40 weight percent crosslinked polymer, and most preferably about 20 to about 35 weight percent crosslinked polymer with the balance being the volatile, low molecular weight silicone oil. Once this initially produced gel is prepared, it is mixed with an additional quantity of a volatile, low molecular weight silicone, i.e. additional component (3) which is possibly different from the component (3) used to prepare the initially produced gel, and subjected to mixing or shearing forces to produce a uniform liquid gel that is from about 1 to about 25 weight percent crosslinked polymer, preferably from about 2 to about 20 weight percent crosslinked polymer, more preferably from about 3 to about 15 weight percent crosslinked polymer, and most preferably from about 3 to about 10 weight percent crosslinked polymer with the balance being the volatile, low molecular weight silicone oils, component (3) or a mixture of compounds satisfying the definition of component (3).

The gel initially produced is sufficiently viscous that liquid flow is not ordinarily observable. As a crosslinked polymeric material, the gel initially produced, having 25 weight percent crosslinked polymer network, has a Durometer hardness number, ASTM D-2240-91,of at least 5, preferably of at least 7, more preferably of at least 10 and most preferably of at least 15. ASTM test numbers for the Durometer hardness test are indicative of a material sufficiently resistant to flow that it may fairly be characterized as a solid.

In recent years, the personal care industry has found that the use of a variety of silicone polymers ranging from very low to very high molecular weight can provide improved product flow and a smooth, non-greasy feel in a wide range of applications. So for example, silicone polymers have been used in formulations for antiperspirant/deodorants, skin lotions, creams, hair care, cosmetics and the like. While these silicone polymers provide the desired performance characteristics to personal care products, they have traditionally required a delivery system that includes non-silicone thickening agents. These non-silicone thickening agents are generally undesirable as they have a negative impact on the desired silicone feel.

Recent technology that teaches the use of crosslinked silicone polymers for thickening agents fails to recognize the need to generate the unique and desirable distribution of crosslinked silicone polymer particles that create superior performance characteristics including the smooth silky feel and high viscosity for optimal thickening effects. This technology does not adequately define a process for generating the most highly desired distribution of these particles.

In addition, some of the processing methods suggested by this technology are limited to only a small range of crosslinked silicone polymer that can be useful in the instant invention. Thus as the nature of the crosslinked silicone polymer changes to provide for the desirable, more efficient use of polymer material, the suggested shearing methods using low levels of compression (colloid mills and the like), mechanical cutting shear (rotor/stator mills) or fracture (hammer mills) fail to provide the desired crosslinked silicone polymer particles of the required size and distribution. Further, they fail to define a method for processing the crosslinked silicone polymer in an economical manner.

Surprisingly a process has been discovered for providing a thickener for carrier silicone oil comprising the use of silicone particles having a unique distribution of particle sizes. Further, it has been discovered that the use of high flow induced shear and particle elongation in addition to providing an economical method for processing crosslinked silicone polymers, also generates a unique and highly desirable particle size distribution that provides the desired smooth, silky feel while maintaining high viscosity and thickening properties. Further this method of processing is applicable to the entire range of desirable crosslinked silicone polymers.

While some of the physical properties of the thickening agent are determined by the chemical structure of the crosslinked silicone polymer, the particle size and distribution are key to the highly desirable thickening (viscosity) and feel properties of the product. The efficient thickening behavior is the result of having large particle sizes present to increase the fluid viscosity. The size of the large particles is limited by the need to avoid particle so large that they form visible balls of gel during application. The superior feel is the result of generating smaller particles that improve lubricity during spreading on the skin. If the crosslinked silicone polymer is degraded to too small particles or to homogeneous fluids, they become undesirably heavy or greasy in feel. Thus preparing an efficient thickening agent with the superior feel requires the ability to generate a wide distribution of particles.

Surprisingly, the use of flow induced shear and particle elongation particularly at high stress levels provides a unique distribution of particle sizes when used to process crosslinked silicone polymers. Where as the normal expectation is to find a monomodal or possibly bimodal distribution of particle sizes when employing stress to break down particles, it is found that particularly high flow induced shear and particle elongation produce multiple distributions of particle sizes.

Earlier experiments have shown that the particles prepared in this invention are not fully swollen in material as dilute as five percent elastomer content and 95% cyclic siloxanes. However, if the elastomer is further diluted below elastomer contents of about three percent, the particle swells to its full extent. Thus the particle sizes reported in this invention demonstrate fully extended particles, while those used in most applications are of proportionally smaller actual volume depending on the available solvent. Since for a given particle composition it is possible to measure how much additional solvent may be absorbed, it is possible to back calculate the particle size for any given concentration once the full extended particle size is known. Further, it is within the scope of this invention to prepare smaller particles at a higher elastomer concentration and then swell them at a later time with additional solvent to achieve a larger particle size.

For the product of this invention, the particle size distribution comprises a multiple series of individual and often overlapping particle size populations. Taken together they provide a broad distribution of both large and small particles that impart both high efficiency and viscosity as well as a good feel and lubricity. The individual particle size populations generally fit a log normal particle size distribution and as measured at full range from an average of about 10 microns to an average of about 600 microns. When for a specific application the particles are not fully swollen, the population of particle sizes, i.e. the particle size distribution, will cover proportionally smaller sizes and with a shift to ranges over lower particle sizes. The particle size distribution comprises a series of multiple, identifiable particle populations ranging from less than about 1 microns on swelling to about 600 microns after swelling. It is preferable for the average particle size range when measured in a fully swollen state to cover from about 1 to about 500 microns, more preferably to include about 1 to about 400 microns region and most preferably to include about 1 to about 300 microns after solvent swelling.

The compositions of the present invention are characterized by being dispersions of an organic polymeric elastomer, preferably a silicone elastomer, in a suitable solvent and having a particle size distribution characterized by the presence of three local maxima in the particle size distribution: 1) a local maximum ranging from about 21 to about 26 microns, 2) a local maximum ranging from about 33 to about 38 microns, and 3) a local maximum ranging from about 50 to 60 microns. As local maxima, these three local maxima appear as identifiable spikes in a plot of population versus particle diameter. It is to be emphasized that the compositions of the present invention may possess more than these three local maxima in a plot of population versus particle size, but the compositions of the present invention always possess these three local maxima. Depending on other features of the particle size distribution, the subjective properties of the composition vary from a so-called stiff creamy feel when the distribution is skewed to higher particle diameters to a light creamy feel when the distribution is centered around these three local maxima to a heavy greasy feel when the distribution is skewed to lower particle diameters. These numbers are specific to the instrumental method of analyzing the particle size distribution, specifically using a Malvern Mastersizer fitted with a 300 mm lens.

The process for making suitable crosslinked silicone polymer particles for use in the current application involves the preparation of a crosslinked silicone polymer, often in a low molecular weight silicone fluid. The material may then be further swollen with additional solvent either the same or different than that used in making the crosslinked silicone polymer. The crosslinked silicone polymer is then subjected to force to break it into small particles often in the presence of additional silicone fluid. It is a discovery of this invention that the superior method of breaking the polymer into small particles is through high flow induced shear. In this method, the slurry is first diluted, including the crosslinked silicone polymer and any additionally desired solvent, and then forced through an orifice under pressure generating flow induced shear and particle elongation. In this method, the flow induced shear and particle elongation occur both as the material passes through the orifice and in the entry region to the orifice. Although some material may be cleaved by hitting the edge of the orifice, it is this flow induced shear and particle elongation that ultimately tears the crosslinked silicone polymer apart and creates small particles.

The magnitude and profile of the flow induced shear in this process is controlled by several parameters including the pressure, orifice geometry and fluid viscosity which in part reflects the temperature, flow and shear characteristics of the fluid. Pressure may be defined as the pressure drop across the orifice. Increasing pressure drop increases the flow induced shear such that the crosslinked silicone polymer is more rapidly torn into the desired particle sizes and with a wider, more desirable distribution of particle sizes. Generally, high flow induced shear is associated with higher pressure drops for a particular orifice geometry and fluid viscosity.

The orifice geometry at a given pressure drop also determines the nature of high flow induced shear. Orifice geometry is a very flexible characteristic with a variety of shapes and sizes. Thus for example, an orifice might have an opening shape that is round, ovoid, rectangular or annular. Such orifices may be completely open or contain a pin or other obstruction at the opening. There may be one opening or many of the same or different geometries. In general as the orifice gets larger at the same pressure and fluid viscosity, the distribution of particle sizes becomes wider and more desirable. Similarly the length of the path traveled by the fluid may be long or short, straight or bent. In general as the length of the orifice becomes shorter, the flow induced shear increases and smaller more widely distributed particles are generated. The orifice size also influences flow induce shear in the entry region to the orifice. Thus as the ratio increases such that the material flows from a larger tube to a smaller orifice the particle size distribution is increased.

Fluid viscosity also determines the flow induced shear. As the viscosity of the fluid increases, the flow induced shear increases with the attendant desirable results. Viscosity will be influenced by the temperature, a lower more constant temperature giving higher viscosity is desirable. Similarly, materials exhibiting shear thinning, as some silicones are known to do, will have a lower flow induced shear in the orifice, thus increasing the particle size and narrowing the distribution. While the viscosity of the initial slurry of elastomer fed to the process may be difficult to measure, after processing the viscosity can be measured and for the first several passes through the process the viscosity of the elastomer dispersion increases. Because the material being processed is a dispersion or suspension of elastomer particles in a solvent, viscosity may be affected by a consideration of the so-called solids level. As the solids level is increased, i.e. the amount of solvent present being progressively reduced, resistance to flow increases, which can sometimes be measured as an increase in viscosity.

Taken together, these parameters are the major factors in determining flow induced shear. Depending upon a particular environment, any one or more of these three may be the dominant, i.e. most critical factor(s), in deciding the actual flow induced shear. High dynamic shear is that which is sufficient to break down the crosslinked particles to the desired size and distribution. In some instances this is accomplished in a single pass through the orifice, or alternatively a few to several passes may be required to achieve the desired particle size. In general fewer passes and wider particle size distribution are the more desired economic and performance results coming from high flow induced shear.

Flow induced particle elongation occurs as the crosslinked silicone polymer converges under pressure as it is forced to flow toward the orifice, flowing from a large diameter environment to the small diameter opening. As the particle travels through this region, it is elongated and smaller particles generated. The critical factors include pressure, fluid viscosity and the ratio of the cross sectional areas of the feed chamber to orifice. As the pressure is increased the particle elongation is increased and more efficient particle size breakage is achieved. Similarly, as the viscosity of the fluid is increased, the particle elongation is increased. As the ratio of the cross sectional areas of the feed chamber to the orifice is increased, the particle elongation is increased. In general as the particle elongation increases the efficiency in breaking down particles increases requiring fewer passes.

The pressure range desirable for sufficient flow induced shear and particle elongation is above 500 psi. Preferably it is above 1000 psi, more preferably over 1500 psi and most preferably over 2000 psi. The viscosity should be above 500 ctks. Preferably is should be over 750 ctks more preferably over 1000 ctks and most preferably over 5000 ctks. The orifice size is limited by the ability of the pumping system to maintain sufficient pressure. As a practical matter it is desirable to have an orifice size of less than 0.5 square inches, preferably less than 0.1 square inches, more preferably less than 0.05 sq. in, and most preferably less than 0.01 sq. inch.

The interaction of all of these operating variables combine to produce a process where the elastomer dispersion is reduced in average particle size and the unique particle size distribution is produced. Generally unless the elastomer dispersion is processed at a very high pressure drop, conversion to a desirable composition is not achieved in a single pass. There is thus a correlation between the applied pressure drop and the number of passes through the processing equipment that the elastomer dispersion must be subjected to in order to convert the material to the desired composition. This is reflected by the following dimensionless correlation equation that determines the number of passes, $N_p$ necessary to produce acceptable material for a given pressure drop, $P_d$:

$$N_p = 82,799 P_d^{(-1.1696)}$$

To some extent this equation is arbitrary and varies as the definition of what constitutes acceptable material. Material possessing a particle size distribution characterized by three peaks or three local maxima in the particle size distribution: 1) a local maximum ranging from about 21 to about 26 microns, 2) a local maximum ranging from about 33 to about 38 microns, and 3) a local maximum ranging from about 50 to 60 microns constitutes material that is acceptable.

Further, it is possible to generate a dimensionless correlation which correlates the resulting average particle size (as determined by a Malvern Mastersizer™), $S_p(avg.)$, with the pressure drop, $P_d$, orifice cross-sectional area, $O_a$, and the number of passes, $N_p$.

$$S_p(avg.) = K + C_1 P_d + C_2 O_a + C_3 N_p,$$

where K is an intercept, and the various $C_i$'s are coefficients associated with the indicated variable, i.e. $C_1$ is the pressure drop coefficient, $C_2$ is the orifice cross-sectional area coefficient, and $C_3$ is the number of passes coefficient. The various operating ranges are defined in the following tables:

TABLE A

| Parameter | Operating Ranges | |
|---|---|---|
| | Minimum (from about) | Maximum (to about) |
| $P_d$ | 500 | 35000 |
| $O_a$ | 0.5 | 0.0001 |
| $N_p$ | 1 | 100 |
| $S_p(avg.)$ | 585 | 16 |
| K | 639 | 639 |
| $C_1$ | −0.026 | 0.026 |

TABLE A-continued

Operating Ranges

| Parameter | Minimum (from about) | Maximum (to about) |
|---|---|---|
| $C_2$ | −61 | −61 |
| $C_3$ | 2.87 | 2.87 |

TABLE B

Preferred Operating Ranges

| Parameter | Minimum (from about) | Maximum (to about) |
|---|---|---|
| $P_d$ | 1000 | 30000 |
| $O_a$ | 0.1 | 0.002 |
| $N_p$ | 1 | 50 |
| $S_p$(avg.) | 3 | 610 |
| K | 639 | 639 |
| $C_1$ | −0.026 | −0.026 |
| $C_2$ | −61 | −61 |
| $C_3$ | 2.87 | 2.87 |

TABLE C

More Preferred Operating Ranges

| Parameter | Minimum (from about) | Maximum (to about) |
|---|---|---|
| $P_d$ | 1500 | 27500 |
| $O_a$ | 0.005 | 0.0003 |
| $N_p$ | 1 | 30 |
| $S_p$(avg.) | 10 | 603 |
| K | 639 | 639 |
| $C_1$ | −0.026 | −0.026 |
| $C_2$ | −61 | −61 |
| $C_3$ | 2.87 | 2.87 |

TABLE D

Most Preferred Operating Ranges

| Parameter | Minimum (from about) | Maximum (to about) |
|---|---|---|
| $P_d$ | 2000 | 25000 |
| $O_a$ | 0.01 | 0.0005 |
| $N_p$ | 1 | 10 |
| $S_p$(avg.) | 18 | 589 |
| K | 639 | 639 |
| $C_1$ | −0.026 | −0.026 |
| $C_2$ | −61 | −61 |
| $C_3$ | 2.87 | 2.87 |

Because the number of passes, $N_p$, correlates with the pressure drop, $P_d$, the equation for the number of passes may be substituted into the average particle size equation. This mathematical substitution underscores the strong pressure drop dependence of the process. Simply stated, the process of the present invention (to yield the composition of the present invention) is a process where an elastomer dispersion is subjected to a pressure and passed through an orifice at a specified pressure drop wherein the average particle size is reduced and the particle size distribution yields certain specified local maxima. Any process that achieves this conversion by means of a pressure drop and an orifice is a process of the present invention. Applicants note that the pressure drop as used herein has the dimensions of pounds per square inch (psi.), the orifice cross-sectional area has the dimensions of square inches (sq. in. or in.$^2$), and particle sizes or average particle size has the dimension of microns.

As the orifice size decreases the pressure must be increased to maintain throughput. For this reason, a smaller orifice size is listed under the column heading "maximum" in describing the ranges, because smaller orifice size and increased pressure create the same global effect.

Finally, it should be emphasized that the intercept and coefficients in the process variable equation may change depending on the specific machine used. The data presented herein represent the results of a correlation on a few selected machines are thus illustrative rather than constituting a definition or limitation. Thus while the process variables are fairly precisely defined, the intercept, K, and the coefficients $C_1$, $C_2$, and $C_3$ are more likely to depart from the values reported herein than would the actual process variables. Irrespective of the actual machine and the actual values of the intercept and these coefficients in a process variable correlation, any process accomplishing the conversion of particle size to that defined herein is intended to be covered by the appended claims.

The generation of the desired particle size is in part determined by the swelling of the particles before application of the flow induced shear and particle elongation. As the particle swells with solvent, internal stress is developed which lowers the level of shear and particle elongation required to tear apart the particle. Thus more swelling or lower crosslinked silicone polymer concentration in the slurry being processed increases the internal stress and makes the process more efficient. It is desirable to dilute to a crosslinked polymer concentration of less than 60% by weight solids. It is preferable to swell and dilute the crosslinked silicone polymer to less than 50% by weight solids, more preferable to swell the crosslinked polymer to less than 40% by weight solids and most preferable to dilute the crosslinked polymer to less than 30% by weight solids content.

The resistance to flow of the initially produced gel is overcome by high speed mixing or shearing wherein the resulting composition or mixture is a uniform liquid and has a viscosity ranging from about 500 to about 150,000 centistokes at 25° C., more preferably the resulting viscosity of the composition or mixture is from about 1,000 to about 100,000 centistokes at 25° C., and most preferably the resulting viscosity of the composition or mixture is from about 10,000 to about 60,000 centistokes at 25° C. By shearing, Applicants mean the imposition of a force upon the composition where the mixture is treated using a two roll mill, a colloid mill, a Gaulin homogenizer, a Sonolator, Ross™ mixer, Aviston™ mixer, Microfluidizer, etc. The elastomer dispersions processed by the process of the present invention are comprised of an elastomer gel and a low molecular weight silicone. The process of the present invention used to achieve the composition of the present invention may be applied to an elastomer dispersion or a dispersion of a gel or a gel. Subjecting these compositions to a shearing force produces a component suitable for use in personal care or cosmetic applications that has an improved spreadability and an improved substance or feel because of the presence of the composition of the present invention possessing a unique particle size distribution.

These materials, either as the silicone itself or a dispersion of the silicone in another suitable solvent may be emulsified to form conventional oil-in-water or water-in-oil emulsions. Typically such emulsification requires the addition of a suitable surfactant. More importantly, these new materials may be emulsified with non-aqueous organic hydroxylic solvents where one of the non-aqueous phases is the continuous phase of the emulsion. Such non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof. The use of these various hydroxylic non-aqueous solvents will affect the aesthetic characteristics of the cosmetic compositions prepared from the non-aqueous emulsion.

The emulsifying agents useful in preparing the emulsions of the present invention are selected from the group consisting of silicone containing emulsifying agents, emulsifying agents derived from sorbitan compounds and emulsifying agents derived from fatty alcohols, more preferably the emulsifying agent is selected from the group consisting of fatty acid esters, sorbitan sesquioleate, sorbitan oleate, sorbitan isostearate, polyglyceryl-3 oleate, alkoxylated alcohols such as laureth-4, laureth-7, deceth-12, steareth-10, hydroxylated or alkoxylated derivatives of silicone compounds such as dimethicone copolyol, cetyl dimethicone copolyol, and lauryl methicone copolyol, glyceryl esters such as polyglyceryl-4-isostearyl and mixtures thereof; and most preferably the emulsifying agent is dimethicone coployol which may or may not be dispersed in a silicone oil or cyclomethicone diluent.

The personal care applications where the emulsions of the present invention may be employed include, but are not limited to, deodorants, antiperspirants, skin creams, facial creams, hair care products such as shampoos, mousses, styling gels, protective creams, such as sunscreen, and color cosmetics such as lip products or lipsticks, foundations, blushes, makeup, and mascara; and other cosmetic formulations where silicone components have been added. These cosmetic compositions will in all probability also contain other materials designed to improve appearance or functionality of the composition and as such cosmetic compositions prepared with the compositions of the present invention may additionally comprise emollients, pigments, colorants, fragrances, preservatives, hormones, medicinal compounds, anti-microbial agents, anti-fungal agents, vitamins, salts, absorbing agents for ultraviolet (UV) radiation and botanical extracts. The compositions of the present invention also have utility as drug delivery systems for topical application of medicinal compositions that are to be applied to the skin.

All United States patents referenced hereinbefore and hereinafter are herewith and hereby incorporated by reference.

Experimental

I. Preparation of Materials

Vinylsilane 1 was prepared by phenethyl alcohol displacement on the corresponding chlorosilane. This vinylsilane was then reacted via a hydrosilylation reaction with $M^HD_{25}M^H$ to give polymer 2.

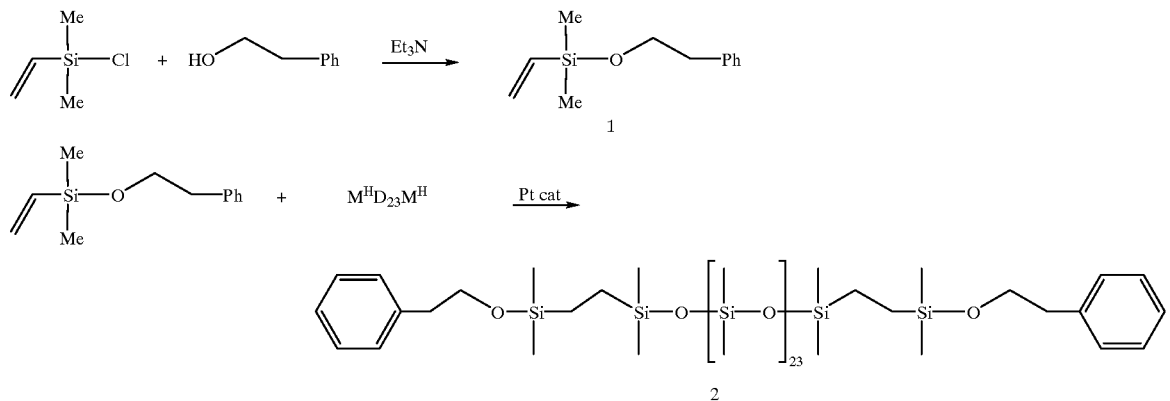

Vinylsilane 4 was prepared by in-situ formation of the enolate of 3, followed by displacement of the chloro group from 5.

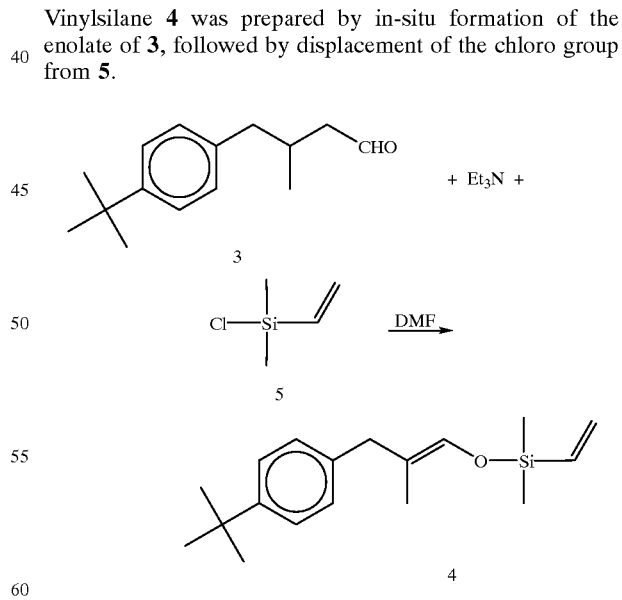

Hydrosilation of 4 onto a hydride terminated polysiloxane gave polymer 6.

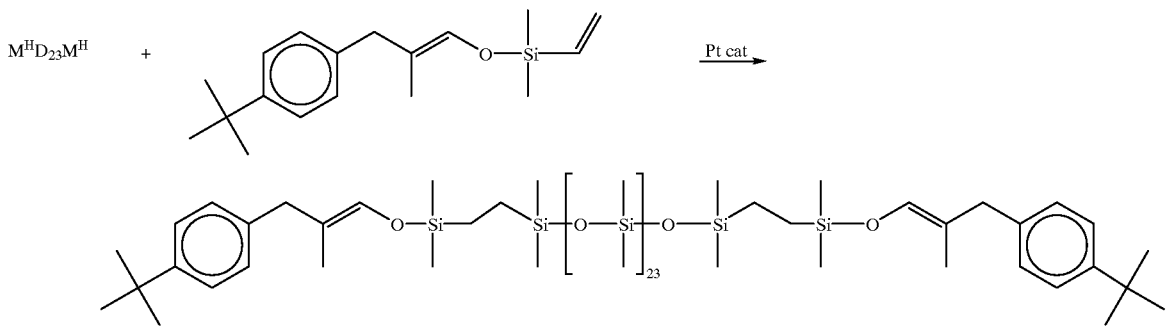

6

Emulsions of the fragrant polymers were prepared by mixing the appropriate polymer with an internal GC standard and nonionic surfactants followed by emulsifying in water.

II. Control Reactions

An emulsion of polymer 2 was held at room temperature for 2 weeks and the amount of free phenethylalcohol found in the emulsion between day 3 and day 14 was constant at 15–17%.

The same emulsion diluted with a mixture of toluene and isopropyl alcohol was found to contain 19–23% free phenethylalcohol between days 3 and 5.

The emulsion was still stable 10 days after being treated with a weakly basic (pH 10) solution of KOH. The amount of free phenethylalcohol was between 7.5 and 12.5%.

III. Release Reactions

When emulsion 2 was treated with an excess of aqueous KOH, rapid release of the fragrance was observed with essentially quantitative release seen in less than 10 min. Concentrated hydrochloric acid gave the same results with quick release of the fragrance.

Examination of organic acids and bases showed that a strong acid like trifluoroacetic acid rapidly effected release of the fragrance. Reactions of emulsified 2 with acetic acid or the organic base triethylamine gave no free phenethylalcohol after 3 h.

With extended periods of time, acetic acid promoted 30% release over 23 h. There was still no evidence of triethylamine catalyzed release of fragrance over this same time period.

With the silylenolether fragrance emulsion 6, treatment with KOH or HCl again resulted in fast release of the fragrance. Trifluoroacetic acid also showed rapid release while acetic acid released fragrance over several days. Again, triethylamine showed little fragrance release.

IV. Preparation

Dimethylvinylsilane 1—A 1000 mL 3-neck round bottom flask equipped with a mechanical stirrer, a thermometer, a condenser and a nitrogen inlet was charged with phenethyl alcohol (124.5 mL, 1.042 moles), triethylamine (155 mL, 1.112 moles) toluene (300 mL) and then dimethylvinylchlorosilane (150 mL, 1.1 moles) was added over 1.5 h. The mixture exothermed to 75° C. and was then kept at 65° C. for and additional 0.5 h. The mixture was filtered, the filter cake washed with toluene, then dried over $MgSO_4$ and stripped on a rotary evaporator and then distilled under vacuum (4 mm Hg/81–85° C.) to give180.5 g (84%) product.

Preparation of Polymer 2—Vinyl silane 1 (102.6 g, 0.497 mole) and a divinyltetramethyldisiloxane platinum complex (30 mL of 5% solution in isopropanol) were heated to 80° C. and then $M^HD_{23}M^H$ (452 g, 0.245 mole) was added slowly over 1.75 h. The reaction was allowed to continue for 17 h then cooled to give polymer 2.

Dimethylvinylsilane 4—A 100 mL 3-neck round bottom flask equipped with a stir-bar, a thermometer, a condenser and a nitrogen inlet was charged with dimethylvinylchlorosilane (4.1 mL, 0.030 moles), 3 (5.0 g, 0.024 moles), triethylamine and N,N-dimethylformamide (DMF, 20 mL) and heated to 80° C. for 22 h. the mixture was diluted with 100 mL of Isopar-C, and the mixture was washed three times with cold saturated aqueous sodium bicarbonate, then cold 1N HCl, then bicarbonate, then dried over $MgSO_4$ and stripped to give 6.4 g (90%) product.

Preparation of Polymer 6—Vinyl silane 4 (5.0 g, 0.017 mole) and a divinyltetramethyldisiloxane platinum complex (2 mL of 5% solution in isopropanol) were heated to 65° C. and then $M^HD_{23}M^H$ (16.0 g, 0.0086 mole) was added slowly over 0.5 h. The reaction was allowed to continue for 5.5 h then cooled to give polymer 6.

Preparation of Emulsified 2—To a glass beaker was added Polymer 2 (50 g) and bibenzyl (1.7 g, an internal GC standard) and mixed until a clear mixture was obtained. The mixture was further mixed with 10 g 70% ethoxylated (30 EO) nonylphenol (T-DET-N-307) and 5 g $C_{11}$–$C_{15}$ secondary alcohol exothylate (Tergitol 15-S-7) followed by 50 g water at room temperature. A white emulsion formed immediately.

Dilution of Emulsified 2—In order to get a representative sample for GC analysis, the emulsion (5 g) was diluted with isopropanol (10 g) and toluene (13.5 g) which gave a homogeneous solution.

KOH Treatment of Emulsified 2—To 5 g of diluted emulsion 2 was added KOH (0.22 g of 20% KOH). The solution was stirred for 5 min. An aliquot taken for GC analysis indicated complete release of the phenethyl alcohol.

HCl Treatment of Emulsified 2—To 5 g of diluted emulsion 2 was added concentrated HCl (2 drops). The solution was stirred for 5 min. An aliquot taken for GC analysis indicated complete release of the fragrant moiety.

Acetic Acid Treatment of Emulsified 2—To 4 g of diluted emulsion 2 was added glacial acetic acid (3 drops). The solution was stirred for 5 min. An aliquot taken for GC analysis indicated no release of the fragrant moiety after 3 h. Another aliquot taken after 23 h showed 30% release.

Trifluoroacetic Acid Treatment of Emulsified 2—To 4 g of diluted emulsion 2 was added trifluoroacetic acid (3 drops). The solution was stirred for 3 min. An aliquot taken for GC analysis indicated total release of the fragrant moiety.

Triethylamine Treatment of Emulsified 2—To 4 g of diluted emulsion 2 was added triethylamine (3 drops). The solution was stirred for 5 min. An aliquot taken for GC analysis indicated no release of the fragrant moiety after 23 h.

Preparation of Emulsified 6—To a glass beaker was added Polymer 6 (5.04 g) and dodecane (0.17 g, an internal GC standard) and mixed until a clear mixture was obtained. The mixture was further mixed with 1.0 g 70% ethoxylated (30 EO) nonylphenol (T-DET-N-307) and 0.5 g $C_{11}$–$C_{15}$ secondary alcohol exothylate (Tergitol 15-S-7) followed by 5.0 g water at room temperature. A white emulsion formed immediately.

Dilution of Emulsified 6—In order to get a representative sample for GC analysis, the emulsion (0.63 g) was diluted with isopropanol (10.5 g) which gave a homogeneous solution.

Acetic Acid Treatment of Emulsified 6—To 4 g of diluted emulsion 6 was added glacial acetic acid (3 drops). The solution was stirred for 5 min. An aliquot taken for GC analysis indicated 10% release of the fragrant moiety after 10 min, 18% after 24 h, 36% after 4 days and 43% after 5 days.

Trifluoroacetic Acid Treatment of Emulsified 6—To 3 g of diluted emulsion 6 was added trifluoroacetic acid (3 drops). The solution was stirred for 3 min. An aliquot taken for GC analysis indicated total release of the fragrant moiety.

Triethylamine Treatment of Emulsified 6—To 4 g of diluted emulsion 6 was added triethylamine (3 drops). The solution was stirred for 5 min. An aliquot taken for GC analysis indicated 10% release of the fragrant moiety in 10 min but further release over 4 days.

KOH Treatment of Emulsified 6—To 3 g of diluted emulsion 6 was added 15% aqueous KOH (3 drops). The solution was stirred for 2 min. An aliquot taken for GC analysis indicated complete release of the fragrant moiety in 5 min.

HCl Treatment of Emulsified 6—To 3 g of diluted emulsion 6 was conc. HCl (2 drops). The solution was stirred for 2 min. An aliquot taken for GC analysis indicated 70% release of the fragrant moiety in 5 min.

Preparation of non-aqueous emulsion of fragrance polymer

To a glass beaker was added 6.25 g of Polymer 2 and 10 g of a 10% (w/w) solution of silicone polyether in decamethylcyclopentasiloxane, and mixed until homogeneous. While mixing, 34.4 g of propylene glycol was slowly added. A white emulsion formed immediately Preparation of non-aqueous emulsion of fragrance polymer/elastomer dispersion To a glass beaker was added 10.0 g of the elastomer dispersion, 2.5 g of Polymer 2, and 20 g of a 10% (w/w) solution of silicone polyether in decamethylcyclopentasiloxane, and mixed until homogeneous. While mixing, 67.5 g of propylene glycol was slowly added. A white emulsion formed immediately. The emulsion has a viscosity of 3400 cps at 22° C.

What is claimed is:

1. A mixture comprising two immiscible liquid phases subject to the limitation that one of the two immiscible liquid phases comprises a fragrance releasing siloxane, wherein the fragrance releasing siloxane has the formula:

$$M_f M_g^F D_h D_i^F T_j T_k^F Q_l$$

where M has the formula $R^7R^8R^9SiO_{1/2}$; $M^F$ has the formula $R^7R^8R^FSiO_{1/2}$; D has the formula $R^{10}R^{11}SiO_{2/2}$; $D^F$ has the formula $R^{10}R^FSiO_{2/2}$; T has the formula $R^{12}SiO_{3/2}$; $T^F$ has the formula $R^FSiO_{3/2}$; and Q has the formula $SiO_{4/2}$ where $R^7$, $R^8$, $R^9$, $R^{10}$, $R^{11}$ and $R^{12}$ are each independently selected for each M, $M^F$, D, $D^F$, T and $T^F$ from the group of one to forty carbon atom monovalent alkyl or alkoxy radicals and one to forty carbon atom monovalent aryl or aryloxy radicals where the subscripts f or g are positive, and one or more of the subscripts h, i, j, k or l are positive, subject to the limitation that one of the subscripts g, i, or k is one or greater than one; where $R^F$ has the formula $(R^1O)_a(R^2O)_b(R^3O)_c(R^4)_d(R^5)_eSiR^U$ with $R^U$ a two to forty atom divalent hydrocarbon radical where $R^1O$, $R^2O$ and $R^3O$ are each independently fragrant alkoxide moieties, derived from the alcohols $R^1OH$, $R^2OH$ and $R^3OH$ wherein $R^1OH$, $R^2OH$ and $R^3OH$ are independently fragrant alcohols that are selected from the group consisting of 3-methyl-5-(2,2,3,-trimethyl-3-cyclopenten-1-yl)-4-penten-2-ol, 2-methylbutanol, 3-pentanol, n-pentanol, 2-pentanol, n-hexanol, 2-methylpentanol, 1-decanol, sandela, nonadyl, dimetol, thymol, 1-heptanol, menthol, eugenol, vanillan, o-vanillan, 4-(p-hydroxyphenyl)-2-butanone, syringealdehyde, prenol, cis-3-hexanol, trans-3-hexanol, cis-4-heptenol, trans-2-octenol, trans-2-cis-6-nonadienol, geraniol, nerol, citronellol, crotyl alcohol, oleyl alcohol, linalool, α-terpineol, β-phenethyl alcohol, cinnamic alcohol, benzyl alcohol, α-methylbenzyl alcohol, nonyl alcohol, 1-octanol, 3-octanol, phenethyl salicylate, hydrocinnamyl alcohol, cis-6-nonen-1-ol, trans-2-nonen-1-ol, methyl salicylate, cis-3-octen-ol, anisyl alcohol, carvacrol, dihydrocarveol, benzyl salicylate, tetrahydrogeraniol, ethyl salicylate, ethyl vanillin, isoeugenol, isopulegol, lauryl alcohol, tetrahydrolinalool and 2-phenoxyethanol, with $R^4$ and $R^5$ selected from the group consisting of monovalent hydrocarbon radicals having from one to forty carbon atoms and monovalent alkoxy radicals having from one to forty carbon atoms, where the subscript a has a value ranging from 1 to 3 and the subscripts b, c, d, and e have values ranging from 0 to 2 subject to the limitation that a+b+c+d+e=3.

2. The mixture of claim 1 wherein said mixture comprises an emulsion.

3. The mixture of claim 2 wherein said emulsion is a microemulsion having an ASTM D871 haze below an upper limit of about 150.

4. The mixture of claim 2 further comprising a cross linked silicone gel having a Durometer hardness number, ASTM D-2240-91,of at least 5.

5. The mixture of claim 4 wherein the cross linked silicone gel having a Durometer hardness of at least 5 additionally possesses a particle size distribution characterized by three peaks or three local maxima in the particle size distribution: 1) a local maximum ranging from about 21 to about 26 microns, 2) a local maximum ranging from about 33 to about 38 microns, and 3) a local maximum ranging from about 50 to 60 microns.

6. The mixture of claim 5 wherein the emulsion comprises water.

7. The mixture of claim 5 wherein the emulsion is a non-aqueous emulsion.

8. cosmetic composition comprising the composition of claim 6.

9. A cosmetic composition comprising the composition of claim 7.

10. A mixture comprising two immiscible liquid phases wherein at least one of the two immiscible liquid phases comprises a fragrance releasing siloxane, wherein the fragrance releasing siloxane has the formula:

$$M_f M_g^F D_h D_i^F T_j T_k^F Q_l$$

where M has the formula $R^7R^8R^9SiO_{1/2}$; $M^F$ has the formula $R^7R^8R^FSiO_{1/2}$; D has the formula $R^{10}R^{11}SiO_{2/2}$; $D^F$ has the formula $R^{10}R^FSiO_{2/2}$; T has the formula $R^{12}SiO_{3/2}$; $T^F$ has the formula $R^FSiO_{3/2}$; and Q has the formula $SiO_{4/2}$ where $R^7$, $R^8$, $R^9$, $R^{10}$, $R^{11}$ and $R^{12}$ are each independently selected for each M, $M^F$, D, $D^F$, T and $T^F$ from the group of one to forty carbon atom monovalent alkyl or alkoxy radicals and one to forty carbon atom monovalent aryl or aryloxy radicals where the subscripts f or g are positive, and one or more of the subscripts h, i, j, k or I are positive, subject to the limitation that one of the subscripts g, i, or k is one or greater than one; where $R^F$ has the formula $(R^1O)_a(R^2O)_b(R^3O)_c(R^4)_d(R^5)_e SiR^U$ with $R^U$ a two to forty atom divalent hydrocarbon radical, where $R^1$, $R^2$ and $R^3$ are derived from the group of fragrant esters, ketones, or aldehydes, each independently having the structure:

$$R^7-CH=C(O-)-R^8,$$

with $R^4$ and $R^5$ selected from the group consisting of monovalent hydrocarbon radical having from one to forty carbon atoms and monovalent alkoxy radicals having from one to forty carbon atoms, where the subscript a has a value ranging from 1 to 3 and the subscripts b, c, d, and e have values ranging from 0 to 2 subject to the limitation that a+b+c+d+e=3; $R^7$ is selected from the group consisting of hydrogen and monovalent hydrocarbon radicals having from one to one hundred carbon atoms and $R^8$ is selected from the group consisting of hydrogen and monovalent hydrocarbon radicals having from one to one hundred carbon atoms where the subscript a has a value ranging from 1 to 3 and the subscripts b, c, d, and e have values ranging from 0 to 2 subject to the limitation that a+b+c+d+e=3.

11. The mixture of claim 10 wherein said mixture comprises an emulsion.

12. The mixture of claim 11 wherein said emulsion is a microemulsion having an ASTM D871 haze below an upper limit of about 150.

13. The mixture of claim 11 further comprising a cross linked silicone gel having a Durometer hardness number, ASTM D-2240-91,of at least 5.

14. The mixture of claim 13 wherein the cross linked silicone gel having a Durometer hardness of at least 5 additionally possesses a particle size distribution characterized by three peaks or three local maxima in the particle size distribution: 1) a local maximum ranging from about 21 to about 26 microns, 2) a local maximum ranging from about 33 to about 38 microns, and 3) a local maximum ranging from about 50 to 60 microns.

15. The mixture of claim 14 wherein the emulsion comprises water.

16. The mixture of claim 14 wherein the emulsion is a non-aqueous emulsion.

17. A cosmetic composition comprising the composition of claim 15.

18. A cosmetic composition comprising the composition of claim 16.

* * * * *